(12) United States Patent
Sulaiman et al.

(10) Patent No.: US 10,507,213 B2
(45) Date of Patent: Dec. 17, 2019

(54) METHOD FOR TREATING CANCER USING A SELENOUREA-COORDINATED GOLD(I)-CARBENE COMPLEX

(71) Applicant: King Fahd University of Petroleum and Minerals, Dhahran (SA)

(72) Inventors: Adam A. A. Sulaiman, Dhahran (SA); Mohammad Altaf, Dhahran (SA); Anvarhusein A. Isab, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 0 days.

(21) Appl. No.: 15/794,044

(22) Filed: Oct. 26, 2017

(65) Prior Publication Data
US 2019/0125757 A1    May 2, 2019

(51) Int. Cl.
*A61K 31/555* (2006.01)
*C07F 1/00* (2006.01)
*A61K 45/06* (2006.01)

(52) U.S. Cl.
CPC ............ *A61K 31/555* (2013.01); *A61K 45/06* (2013.01); *C07F 1/00* (2013.01)

(58) Field of Classification Search
CPC .................................................... A61K 31/555
USPC ......................................................... 514/184
See application file for complete search history.

(56) References Cited

FOREIGN PATENT DOCUMENTS

| JP | 5800895 | 9/2015 |
|---|---|---|
| WO | 2014/048480 | 4/2014 |
| WO | 2014/075394 | 5/2014 |
| WO | 2017/075704 | 5/2017 |

OTHER PUBLICATIONS

Seliman et al (Polyhedron, 2017; 137:197-206, available online Aug. 12, 2017) (Year: 2017).*
Weaver et al (Chem Eur J, 2011; 17:6620-6624) (Year: 2011).*
Nahra et al (ChemCatChem, 2015; 7:240-244). (Year: 2015).*
Gura et al (Science, 1997, 278:1041-1042) (Year: 1997).*
Johnson et. al. (British Journal of Cancer, 2001, 84:1424-1431). (Year: 2001).*
Scott R. Patrick, "Synthesis and Reactivity of Novel (NHC)Gold(I) Complexes," University of St. Andrews, 2014, 1 Page.
David J. Nelson et al., "Exploring the Coordination of Cyclic Selenoureas to Gold(I)," Organometallics, 2014, vol. 33, No. 13, 1 Page.
Frauke Marie Hackenberg, "Carbene-Metal Complexes as Anticancer and Antibacterial Drug Candidates," University College Dublin, School of Chemistry and Chemical Biology, 2013, 219 Pages.

* cited by examiner

*Primary Examiner* — Marcos L Sznaidman
*Assistant Examiner* — Rayna Rodriguez
(74) *Attorney, Agent, or Firm* — Oblon, McClelland, Maier & Neustadt, L.L.P.

(57) ABSTRACT

Gold(I)-carbene complexes having a selenium donor ligand with anti-cancer activity and a method of treating cancer. Methods of treating cancer comprising administering the complexes are also provided.

5 Claims, 5 Drawing Sheets

Complex (1)

METHOD FOR TREATING CANCER USING A SELENOUREA-COORDINATED GOLD(I)-CARBENE COMPLEX

BACKGROUND

Field of the Invention

The present disclosure relates to gold(I)-carbene complexes having a selenium donor ligand with anti-cancer activity and to a method for treating or inhibiting cancer.

Description of Related Art

The "background" description provided herein is for the purpose of generally presenting the context of the disclosure. Work of the presently named inventor(s), to the extent it is described in this background section, as well as aspects of the description which may not otherwise qualify as prior art at the time of filing, are neither expressly or impliedly admitted as prior art against the present invention.

In recent years, gold(I) complexes of N-heterocyclic carbenes NHCs) have been studied extensively as prospective anticancer drug candidates. Several of them were found to exhibit remarkable cytotoxic properties, particularly in cisplatin-resistant cell lines. See B. Bertrand, A. Casini, A golden future in medicinal inorganic chemistry: the promise of anticancer gold organometallic compounds, Dalton Trans. 43 (2014) 4209-4219: Weaver, S. Gaillard, C. Toye, S. Macpherson, S. P. Nolan, A. Riches, Cytotoxicity of Gold(I) N-Heterocyclic Carbene Complexes Assessed by Using Human Tumor Cell Lines, Chem.-Eur. J. 17 (2011) 6620-6624; Y. Li, G.-F. Liu, C.-P. Tan, L.-N. Ji, Z.-W. Mao, Antitumor Properties and Mechanisms of Mitochondria-Targeted Ag(I) and Au(I) Complexes Containing N-Heterocyclic Carbenes Derived From Cyclophanes, Metallomics 6 (2014) 1460-1468; H. Sivaram, J. Tan, H. V. Huynh, Syntheses, Characterizations, and a Preliminary Comparative Cytotoxicity Study of Gold(I) and Gold(III) Complexes fearing Benzimidazole- and Pyrazole-Derived N-Heterocyclic Carbenes, Organometallics, 31 (2012) 5875-5883; A. Pratesi, D. Cirri, M. D. Duovic, S. Pillozzi, G. Petroni Z. D. Bugareic, L. Messori gold carbene complexes as candidate anticancer agents, Biometals 29 (2016) 905-911; P. J. Barnard, M. V. Baker, S. J. Berners-Price, A. D. Day, Mitochondrial permeability transition induced by dinuclear gold (I)-carbene complexes: potential new antimitochondrial antitumor agents, J. Inorg. Biochem. 98 (2004) 1642-1647; L. Messori, L. Marchetti, L. Massai, F. Scaletti, A. Guerri, I. Landini, S. Nobili, G. Perrone, E. Mini, P. Leoni, M. Pasquali, C. Gabbiani, Chemistry and Biology of Two Novel Gold(I) Cab Complexes as Prospective Anticancer Agents, Inorg. Chem. 53 (2014) 2396-2403; E. Schuh, Pfluger, A. Citta, A. Folda, M. P. Rigobello, A. Bindoli, A. Casini, F. Mohr, Gold(I) Carbene Complexes Causing Thioredoxin 1 and Thioredoxin 2 Oxidation as Potential Anticancer Agents, J. Med Chem. (2012) 5518-5528; R. Rubbiani, E. Schuh, A. Meyer, J. Lemke, J. Wimberg, N. Metzler-Nolte, F. Meyer, F. Mohr, I. Ott, TrxR inhibition and antiproliferative activities of structurally diverse gold N-heterocyclic carbene complexes, Med. Chem. Commin. 4 (2013) 942-948; M. Altaf, M. Monim-ul-Mehboob, M. Ogasawara N. Casagrande, M. Celegato, C. Borghese, Z. H. Siddik, D. Aldinucci, A. A. Isab, New bipyridine gold(III) dithiocarbamate-containing complexes exerted a potent anticancer activity against cisplatin-resistant cancer cells independent of p53 status, Oncotarget, 18 Nov. 2016 DOI: 10.18632/ oncotarget.13448; B. Bertrand, A. Citta, I. L. Franken, M. Picquet, A. Folda, V. Scalcon, M. P. Rigobello, P. Le Gendre, A. Casini, E. Bodio, Gold(I) NHC-based homo- and hetero-bimetallic complexes, J. Biol. Inorg. Chem. 20 (2015) 1005-1020; T. J. Siciliano, M. C. Deblock, K. M. Hindi, S. Durmus, M. J. Panzner, C. A. Tessier, W. J. Youngs, Synthesis and anticancer properties of gold(I) and silver(I) N-heterocyclic carbene complexes, J. Organomet. Chem. 696 (2011) 1066-1071; B. Bertrand, L. Stefan, M. Pirrotta, D. Monchaud, Bodio, P. Richard, P. Le Gendre, E. Warmerdam, M. H. de Jager, G. M. M. Groothuis, M. Picquet, A. Casini, Caffeine-Based Gold(I)-N Heterocyclic Carbenes as Possible Anticancer Agents: Synthesis and Biological Properties, Inorg. Chem, 53 (2014) 2296-2303; B. K. Rana, A. Nandy, V. Bertolasi, C. W. Bielawski, K. D. Saha, J. Dinda, Novel Gold(I)- and Gold(III)-N-Heterocyclic Carbene Complexes: Synthesis and Evaluation of Their Anticancer Properties, Organometallics, 33 (2014) 2544-2548; M. Altaf, M. Monim-ul-Mehboob, A. A. A. Seliman, A. A. Isab, V. Dhuna, G. Bhatia, K. Dhuna, Synthesis, X-ray Structures, Spectroscopic Analysis and Anticancer Activity of Novel Gold(I) Carbene Complexes, J. Organomet. Chem. 765 (2014) 68-79: Benoit Bertrand, Ewen Bodio, Philippe Richard, Michel Picquet, Pierre Le Gendre, Angela Casini, Gold(I) N-heterocyclic carbene complexes with an "activable" ester moiety: Possible biological applications, J Organomet. Chem. 775 (2015) 124-129, each incorporated herein by reference in their entirety. The advantage of employing carbenes is that they make the resulting complexes more lipophilic and more stable with respect to ligand exchange reaction. See D. Marchione, L. Belpassi, G. Bistoni, A, Macchioni, F. Tarantelli, D. Zuccaccia, The Chemical Bond in Gold(I) Complexes with N-Heterocyclic Carbenes. *Organometallics,* 33 (2014) 4200-4208; D. Benitez, N. D. Shapiro, F Tkatchouk, Y. Wang, W. A. Goddard, F. D. Toste, A bonding model for gold(I) carbene complexes, Nature Chem. 1 (2009) 482-486; and L. N. D. S. Comprido, J. E. M. N. Klein, Cr. Knizia, J. Kastner, A. S. K. Hashmi, The Stabilizing Effects in Gold Carbene Complexes, Angew. Chem. Int. Ed., 54, 2015, 10336-10340, each incorporated herein by reference in their entirety. The lipophilicity of complexes can be tuned by varying the substituents on imidazole group. The presence of an ancillary ligand such as, chloride, phosphine or thiol makes the complex more prone to ligand substitution reactions required for binding to the cellular targets. See P. J. Barnard et at: R. Rubbiani E. Schuh, A. Meyer, J. Lemke, J. Wimberg, N. Metzler-Nolte, F. Meyer, F. Mohr, I. Ott, TrxR inhibition and antiproliferative activities of structurally diverse gold N-heterocyclic carbene complexes, Med. Chem. Commun. 4 (2013) 942-948; R. Rubbiani, S. Can, I. Kitanovic, H. Alborzinia, M. Stefanopoulou, M. Kokoschka, S. Mönchgesag, W. S. Sheldrick, S. Wölfl, I. Ott, Comparative in Vitro Evaluation of N-Heterocyclic Carbone Gold(I) Complexes of the Benzimidazolylidene Type, *J. Med. Chem.* 54 (2011) 8646-8657; M. V. Baker, P. J. Barnard, S. J. Berners-Price, S. K. Brayshaw, J. L. Hickley, B. W. Skelton, A. H. White, Cationic, linear Au(I) N-heterocyclic carbene complexes: synthesis, structure and anti-mitochondrial activity, Dalton Trans. (2006) 3708-3715; J. L. Hickey, R. A. Ruhayel, P. J. Barnard, M. V. Baker, S. J. Berners-Price, A. Filipovska, Mitochondria-Targeted Chemotherapeutics: The Rational Design of Gold(I) N-Heterocyclic Carbene Complexes That Are Selectively Toxic to Cancer Cells and Target Protein Selenols in Preference to Thiols, *J. Am. Chem. Soc.* 130 (2008) 12570-12571, each incorporated herein by reference in their entirety. With respect to the mechanism of antitumor action of gold(I) complexes, mitochondria involving selenoenzyme, thioredoxin reductase (TrxR) have been identified as the potential target sites. Se. Y. Li et al.; P. J. Barnard, M. V. Baker, S. J. Berners-Price, A. D. Day, Mitochondrial permeability transition induced by dinuclear gold(I)-carbene complexes: potential new antimitochondrial antitumor, agents, J. Inorg. Biochem. 98 (2004) 1642-1647; L. Messori et al.; E. Schuh et al.; R. Rubbiani, E. Schuh, A. Meyer, J. Lemke, J. Wimberg, N. Metzler-Nolte, F. Meyer, F. Mohr, I. Ott, TrxR inhibition and antiproliferative activities of structurally diverse gold N-heterocyclic carbene complexes, Med. Chem. Commun. 4 (2013) 942-948; M. V. Baker, P. J. Barnard S. J. Berners-Price, S. K. Brayshaw, J. L. Hickley, B. W. Skelton, A. H. White, Cationic, linear Au(I) N-heterocyclic carbene complexes: synthesis, structure and anti-mitochondrial activity, Dalton Trans. (2006) 3708-3715; J. L. Hickey, R. A. Ruhayel, P. J. Barnard, M. V. Baker, S. J. Berners-Price, A, Filipovska, Mitochondria-Targeted Chemotherapeutics: The Rational Design of Gold(I) N-Heterocyclic Carbene Complexes That Are Selectively Toxic to Cancer Cells and Target Protein Selenols in Preference to Thiols, *J. Am. Chem. Soc.* 130 (2008) 12570-12571, each incorporated herein by reference in their entirety. The inhibition of the activity of thioredoxin reductase (TrxR) is associated with induction of apoptosis in cancer cells. Several gold-NHC complexes as potent inhibitors of TrxR show strong antiproliferative effects on a broad spectrum of tumor cells. See E. Schuh et al.; R. Rubbiani, E. Schuh, A. Meyer, J. Lemke, J. Wimberg, N. Metzler-Nolte, F. Meyer, F. Mohr, I. Ott, TrxR inhibition and antiproliferative activities of structurally diverse gold. N.-heterocyclic carbene complexes, Med. Chem. Commun. 4 (2013) 942-948; M. V. Baker et al.; J. L. Hickey et al.; X. Cheng, P. Holenya, S. Can, H. Alborzinia, R. Rubbiani, I. Ott, S. Wolfl, Mol. Cancer, 13; 2014, 221. A TrxR inhibiting gold(I) NHC complex induces apoptosis through ASKI-p38-MAPK signaling in pancreatic cancer cells, each incorporated herein by reference in their entirety.

The crystal structure studies on gold(I)-carbene complexes reveal a typical linear (quasi) geometry for the central gold atom. See H. Sivaram et al.; T. J. Sicilian et al.; B. Bertrand, L. Stefan, M. Pirrotta, D. Monchaud, E. Bodio, P. Richard, P. Le Gendre, E. Warmerdam, M. H. de Jager, G. M. M. Croothuis, M. Picquet, A. Casini, Caffeine-Based Gold(I)-N-Heterocyclic Carbenes as Possible Anticancer Agents: Synthesis and Biological Properties, Inorg. Chem. 53 (2014) 2296-2303; B. K. Rana et al.; M. Altaf et al.; Benoit Bertrand et al.; P. J. Barnard, M. V. Baker, S. J. Berners-Price, B. W. Skelton, A. H. White, Dinuclear gold(I) complexes of bridging bidentate carbene ligands: synthesis, structure and spectroscopic characterization, Dalton Trans. (2004) 1038-1047; G. Raubenheimer, L. Lindeque and S. Cronje, Synthesis and characterization of neutral and cationic diamino carbene complexes of gold(I), J. Organomet. Chem, 1996, 511, 177-184; M. Z. Ghdhayeb, R. A. Hague, S. Budagumpi, Synthesis, characterization and crystal structures of silver(I)- and gold(I)-N-heterocyclic carbene complexes having benzimidazol-2-ylidene ligands, J. Organomet. Chemistry 757 (2014) 42-50; E. Deck, K. Reiter, W. Moppet, F. Breher A Dinuclear Gold(I) Bis(Carbene) Complex Based on a Ditopic Cyclic (Aryl)(Amino)Carbene Framework, Z, Anorg, Allg. Chem. 642 (2016) 1320-1328; P. de Fremont, N. M. Scott, E. D. Stevens, S. P. Nolan, Synthesis and structural characterization of N-heterocyclic carbene gold(I) complexes, Organometallics 24 (2005) 2411-2418; M. R. Fructos, T. R. Belderrain, P. de Fremont, N. M. Scott, S. P. Nolan, M. M. Diaz-Requejo, P. J. Perez, A Gold Catalyst for Carbene-Transfer Reactions from Ethyl Diazoacetate, Angew. Chem, Int. Ed. 44 (2005) 5284-5288; S. Gaillard, A. M. Z. Slawin, S. Nolan. N-heterocyclic carbene gold hydroxide complex: a golden synthon, Chem. Commun., 2010, 46, 2742-2744; and A. Gomez-Suarez, R. S. Ramon, A. M. Z. Slawin, S. P. Nolan, Synthetic Routes to [Au(NHC)(OH)] (NHC=N-heterocyclic carbene complexes, Dalton Trans., 2012, 41, 5461-5463, each incorporated herein by reference in their entirety. A number of gold(I) complexes based on diisopropylphenyl derivative of carbene (1,3-bis(2,6-di-isopropylphenyl)imidazol-2-ylidene, Ipr) have been reported and some of them were investigated for the anticancer properties. See J. Weaver et al.; M. Altaf et al.; P. J. Barnard, M. V. Baker, S. J. Berners-Price, B. W. Skelton, A. H. White, Dinuclear gold(I) complexes of bridging bidentate carbene ligands: synthesis, structure and spectroscopic characterization, Dalton Trans. (2004) 1038-1047; P. de Fremont et al.; M. R. Fructos et al.; S. Gaillard et al.; and A, Gomez-Suarez et al., each incorporated herein by reference in their entirety. The presence of isopropyl groups on carbene might increase the lipophilicity of the resulting complex and thereby enhance its cytotoxicity. See J. Weaver et al.; P. J. Barnard, M. V. Baker, S. J. Berners-Price, A. D. Day, Mitochondrial permeability transition induced by dinuclear gold(I)-carbene complexes: potential new antimitochondrial antitumor agents, J. Inorg. Biochem. 98 (2004) 1642-1647; and M. V. Baker, P. J. Barnard, S. J. Berners-Price, S. K. Brayshaw, J. L. Hickley, B. W. Skelton, A. H. White, Cationic, linear Au(I) N-heterocyclic carbene complexes: synthesis, structure and anti-mitochondrial activity Dalton Trans (2006) 3708-3715, each incorporated herein by reference in their entirety. The crystal structures and anticancer properties of Ipr-Au-dithiocarbamate complexes have been reported. M. Altaf et al., incorporated herein by reference in its entirety.

However, so far, there is no known report in the literature on Au-carbene complexes having a selenium donor ligand.

The inventors disclose synthesis, spectral characterization, and crystal structure of a gold(I)-carbene complex containing selenourea as a co-ligand. The interaction of this complex with L-tryptophan and L-tyrosine was investigated. Moreover, the cytotoxic activity of this gold (I) complex was determined against three distinct human cancer cell lines MCF7 (breast cancer), HCT15 (colon cancer) and A549 (lung carcinoma) cell lines.

BRIEF SUMMARY OF THE INVENTION

The following provides a summary of certain exemplary embodiments of the present invention. This summary is not an extensive overview and is not intended to identify key or critical aspects or elements of the present invention or to delineate its scope.

The invention is directed to gold(I) complexes with selenones and to methods of treating cancer using these complexes. One example of such a gold(I)selenone complex is Complex (I) [Au(Ipr)(Seu)]PF$_6$. The invention includes the exemplified complexes as well as their structural variants, for example, complexes having additional rum-hydrogen ring substituents or anions other than chloride.

BRIEF DESCRIPTION OF THE DRAWINGS

FIG. 3A (HCT15, colon cancer cells). FIG. 3B (A549 cells, lung carcinoma cells) and FIG. 3C (MCF7 cells, breast cancer cells).

DETAILED DESCRIPTION OF THE INVENTION

Figure 1:
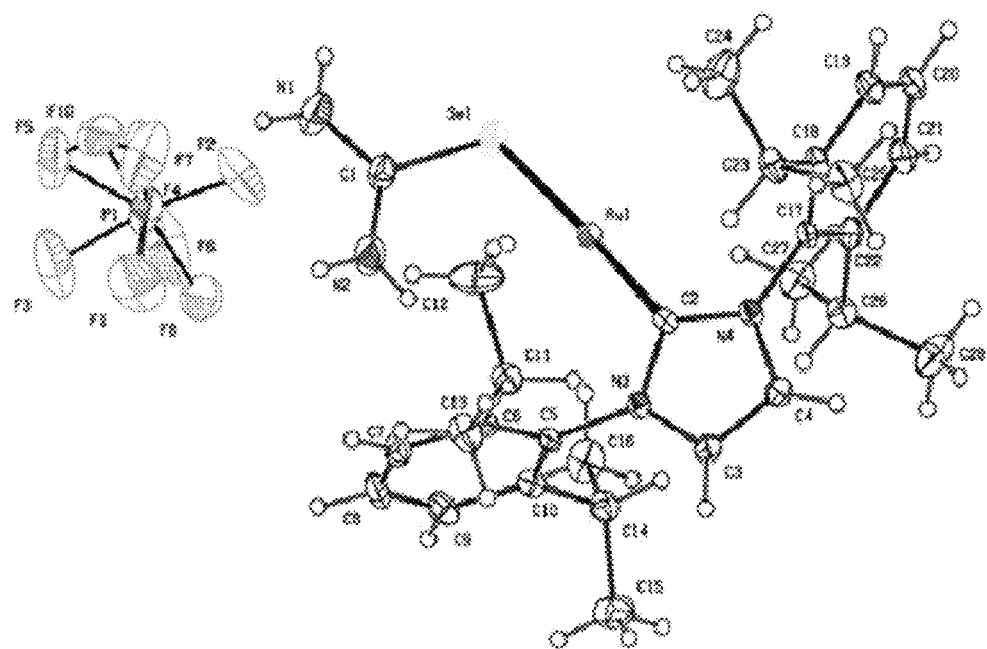
FIG. 1. The molecular structure of [Au(Ipr)(Seu)]PF$_6$ (1) with atom labeling. The displacement ellipsoids are drawn at the 30% probability level.

The present disclosure will be better understood with reference to the following definitions:

Gold(I) describes gold in an, oxidation state of +1. One example of a gold(I) compound is gold(I) chloride having the formula AuCl. In contrast, gold(III) is in an oxidation state of 3', for example, in gold(III) chloride which has the formula Au$_2$Cl$_6$.

An n-heterocyclic carbene or NHC is a divalent ligand having the general structure:

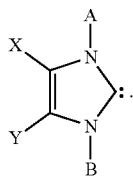

NHCs can complex with low and high valent transition metals like gold (Au) via stable metal-carbene bonds and provide a complex with high thermal and hydrolytic durability. Large scale production of NHCs is easy. Additional background information about NHCs and a description of how NHCs are made may be found in the text available at www.princeton.edu/chemistry/macmillan/group-meetings/Nikki_NHC.pdf (last accessed Oct. 9, 2017, incorporated by reference).

Selenourea or Seu is an organoselenium compound with the formula SeC(NH$_2$)$_2$. It is commercially available and can be used as a precursor in the synthesis of selenium-containing heterocycles, which exhibit anti-inflammatory and anti-cancer activity. In addition, selenourea is used in redox systems containing biological oxidizing agents such, as hydroxyl radicals (.OH), singlet oxygen ($^1$O$_2$), hydrogen peroxide (H$_2$O$_2$), and peroxynitrite (ONOO) to produce particles of elemental nanoselenium. Selenourea has been used as a radioprotector in several in vivo systems.

Other selenourea-type compounds include:

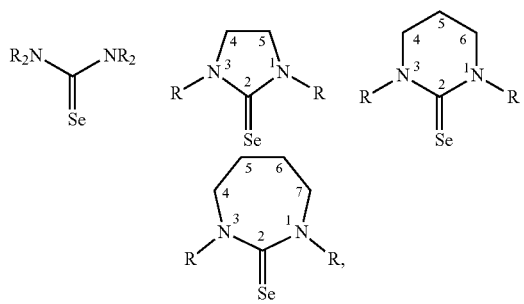

wherein the R groups as well as substituents to positions 4, 5, 6 or 7 are, independently, hydrogen, alkyl, aryl, —OH, or —O-alkyl or another substituent suitable for producing an active Au(I) complex.

It is disclosed herein that selenourea in combination with a gold(I) complex precursor such as NHC-Au—Cl produces a complex having potent antitumor activity compared to the precursor. While not being bound to any particular scientific theory, this could be due to improved uptake of gold(I) complexes containing selenourea or intracellular interactions between the complex or its components.

The term anion or counter-anion refers to an anion, preferably a pharmaceutically acceptable anion, that is associated with a positively charged gold(I) carbene complex. Non-limiting examples of pharmaceutically counter-anions include nitrate, halides such as fluoride, chloride, bromide, iodide; nitrate; sulfate; phosphate; amide; methanesulfonate; ethanesulfonate; p-toluenesulfonate, salicylate, maleate, maleate, succinate, tartrate; citrate; acetate; perchlorate; trifluoromethanesulfonate (triflate); acetylacetonate; hexafluorophosphate; and hexafluoroacetylacetonate. Use of PF$_6^-$ as a counterion facilitates the water solubility of a gold(I) carbene, which is not possible for cisplatin or transplatin.

Hexafluorophosphate or PF$_6^-$ is one type of counteranion which may be incorporated into the gold(I) complexes of the invention. This octahedral species is isoelectronic with sulfur hexafluoride, SF$_6$, and the hexafluorosilicate dianion, SiF$_6^{2-}$, and is valence isoelectronic with the highly stable superacid anion fluoroantimonate SbF$_6^-$. Some embodiments of the invention contain one or more counterions other than PF$_6^-$.

Compound of Complex. As used herein, "compound" and "complex" (or by numeric designation such "1" for Complex 1) are used interchangeably and are intended to refer to a chemical entity, whether in the solid, liquid or gaseous phase, and whether in a crude mixture or in purified or isolated form.

Figure 6:
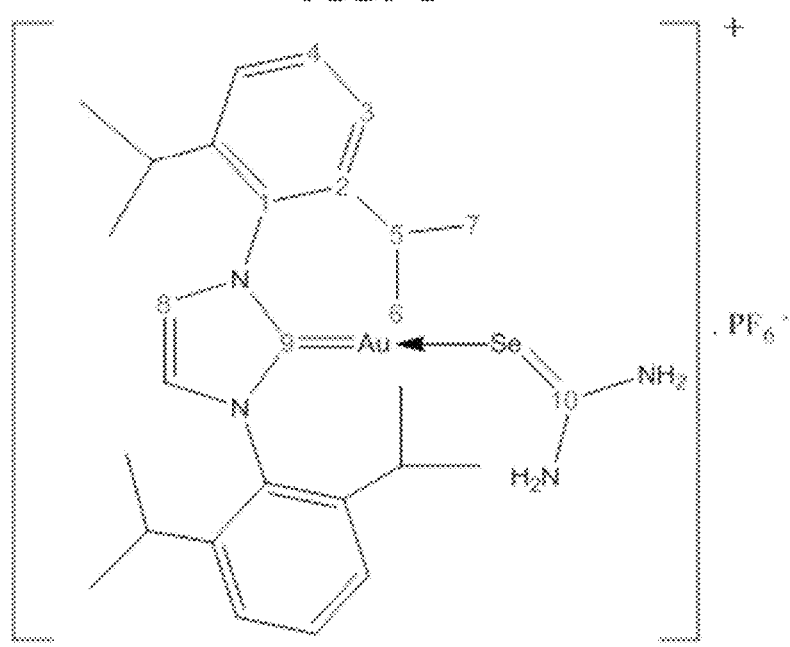
FIG. 6. Structure of [Au(IPr)(Seu)]PF$_6$ (1) and its resonance assignment.

In complexes of the invention an Au atom is directly bound to the selenourea ligand As shown in the embodiment of FIG. 6, an N-heterocyclic carbene ("NHC") is bound to a gold(I) ion at position 9 and carbon-carbon double bond may be present at position 8 as shown for Complex (1).

The precursor used to prepare Complex 1 of the invention is NHC-Au—Cl, which has Cl bound to Au(I) but which has very low anti-tumor activity compared to Complex 1. Complex 1 has potent anti-tumor activity due to the selenourea ligand which that may be due in part to uptake or intracellular interactions.

The coordination of NHC-Au with selenium ligands is important from the biochemical point of view because selenocysteine is present at the active site of the thioredoxin reductase enzyme which is considered as the possible biological target for anticancer gold compounds. When coordinated with selenourea the gold(I) complex is stable under physiological conditions from oxidation to Au(III) or reduction to Au(0) and is stable in polar solvents such as water, methanol, ethanol, acetone as well as in deuterated solvents like dichloromethane.

A gold(I) complex of the invention is described by general Formula (I) below:

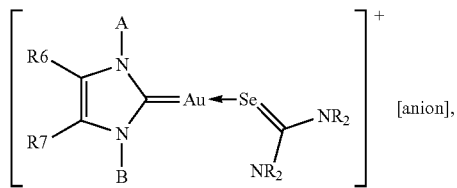

Formula (I)

where A and B are 5, 6, 7, or 8-membered rings which may be unsubstituted or substituted aromatic or heteroaromatic rings and R6 and R7 are hydrogen or other non-hydrogen substituents described herein.

Other embodiments of the complex are described by Formula (2) in which A and B are six-membered aromatic rings, for example bis-phenyl as shown by Formula (2) below:

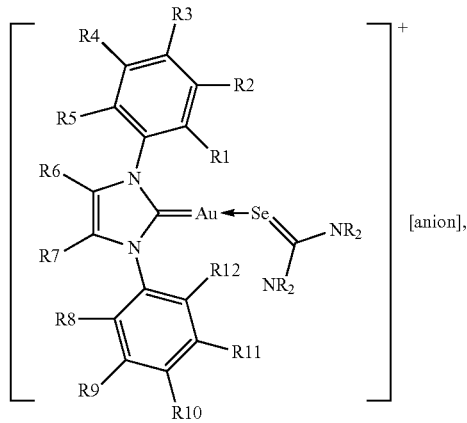

Formula (2)

and R1-R12 are, independently, selected from hydrogen, halogen, hydroxyl, amino, nitro, cyano, optionally substituted alkyl, an optionally substituted cycloalkyl, optionally substituted heterocyclyl, optionally substituted arylalkyl, optionally substituted heteroaryl, optionally substituted alkoxyl, optionally substituted aryl, optionally substituted alkenyl, N-monosubstituted amino group, or N,N-disubstituted amino group; and [anion] may be at least one pharmaceutically acceptable anion, preferably $PF_6^-$; and wherein R in $NR_2$ is independently hydrogen, $C_1$-$C_6$ alkyl, another suitable substituent, or bond; and wherein the two $NR_2$ groups in the selenourea-type molecule may together with two or more intervening carbon or heteroatoms form a 5, 6, 7 or 8-membered ring.

Other substituents that may appears on the 5 to 8-membered rings of Formula (1) or at positions R1-R12 in Formula (2) as $NR_2$ group substituents) include, but are not limited to, those defined below.

The term "alkyl", as used herein, unless otherwise specified, refers to a straight or branched hydrocarbon fragment such as a $C_1$-$C_6$ group. Non-limiting examples of such hydrocarbon fragments include methyl, ethyl, propyl, isopropyl butyl, isobutyl, t-butyl, pentyl, isopentyl, neopentyl, hexyl, isohexyl, 3-methylpentyl, 2,2-dimethylbutyl, and 2,3-dimethylbutyl. As used herein, the term "cycloalkyl" refers to a cyclized alkyl group. Exemplary cycloalkyl groups include, but are not limited to, cyclopropyl, cyclobutyl, cyclopentyl, cyclohexyl, norbornyl, and adamantyl. Branched cycloalkyl groups, for example, 1-methylcyclopropyl and 2-methycyclopropyl groups, are included in the definition of cycloalkyl as used in the present disclosure. The term "alkenyl" refers to a straight, branched, or cyclic hydrocarbon fragment containing at least one C=C double bond. Exemplary alkenyl groups include, without limitation, 1-propenyl, 2-propenyl (or "allyl"), 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-ocentyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, and 9-decenyl. The term "aryl", as used herein, and unless otherwise specified, refers to phenyl, biphenyl, naphthyl, anthracenyl, and the like. The term "heteroaryl" refers to an aryl group where at least one carbon atom is replaced with a heteroatom (e.g., nitrogen, oxygen, sulfur) and can be indolyl, furyl, imidazolyl, triazolyl, triazinyl, oxazolyl, isoxazolyl, thiazolyl, isothiazolyl, pyrazolyl, pyrrolyl, pyrazinyl, tetrazolyl, pyridyl (or its N-oxide), thienyl, pyrimidinyl (or its N-oxide), IH-indolyl, isoquinolyl (or its N-oxide), or quinolyl (or its N-oxide), for example. As used herein, the term "substituted" refers to at least one hydrogen atom that is replaced with a non-hydrogen group, provided that normal valencies are maintained and that the substitution results in a stable compound. When a compound or a R group is noted as "optionally substituted", the substituents are selected from the exemplary group including, but not limited to, aroyl (as defined hereinafter); halogen (e.g., chlorine, bromine, fluorine or iodine); alkoxy (i.e., straight or branched chain alkoxy having 1 to 10 carbon atoms, and includes, for example, methoxy, ethoxy, propoxy, isopropoxy, butoxy, isobutoxy, sec-butoxy, tert-butoxy, pentoxy, isopentoxy, hexyloxy, heptyloxy, octyloxy, nonyloxy, and decyloxy); cycloalkyloxy including cyclopentyloxy, cyclohexyloxy, and cycloheptyloxy; aryloxy including phenoxy and phenoxy substituted with halogen, alkyl, alkoxy, and haloalkyl (which refers to straight or branched chain alkyl having 1 to 8 carbon atoms which are substituted by at least one halogen, and includes, for example, chloromethyl, bromomethyl, fluoromethyl, iodomethyl, 2-chloroethyl, 2-bromoethyl, 2-fluoroethyl, 3-chloropropyl, 3-bromopropyl, 3-fluoropropyl, 4-chlorobutyl, 4-fluorobutyl, dichloromethyl, dibromomethyl, difluoromethyl, diiodomethyl, 2,2-dichloroethyl, 2,2-dibromoethyl, 2,2-difluoroethyl, 3,3-dichloropropyl, 3,3-difluoropropyl, 4,4-dichlorobutyl, 4,4-difluorobutyl, trichloromethyl, trifluorormethyl, 2,2,2-tri-fluoroethyl, 2,3,3-trifluoropropyl, 1,1,2,2-tetrafluoroethyl, 2,2,3,3-tetrafluoropropyl), hydrocarbyl; arylalkyl; hydroxy; alkoxy; oxo; alkanoyl; alkanoyloxy; amino; alkylamino; arylamino; arylalkylamino; disubstituted amines (e.g. in which the two amino substituents are selected from the exemplary group including, but not limited to, alkyl, aryl, or arylalkyl); alkanoylamino; thiol; alkylthio; arylthio; arylalkylthio; alkylthiono; arylthiono; aryalkylthiono; alkylsulfonyl; arysulfonyl; arylalkylsulfonyl; sulfonamido (e.g., —SO₂NH₂); substituted sulfonamide; nitro; cyano; carboxy; carbamyl (e.g., —CONH₂, —CONHalkyl, —CONHaryl, —CONHarylalkyl or cases where there are two substituents on one nitrogen from alkyl, aryl, or arylalkyl); alkoxycarbonyl; aryl; heteroarylcarbonyl; heterocyclyl; and mixtures thereof and the like. The substituents may be either unprotected, or protected as necessary, as known to those skilled in the art, for example, as taught in Greene, et al., "Protective Groups in Organic Synthesis", John Wiley and Sons, Second Edition, 1991, hereby incorporated by reference in its entirety). The term "heterocyclyl" as used in this disclosure refers to a 3-8, preferably 4-8, more preferably 4-7 membered monocyclic ring or a fused 8-12 membered bicyclic ring which may be saturated or partially unsaturated, which monocyclic or bicyclic ring contains 1 to 4 heteroatoms selected from oxygen, nitrogen, silicon, or sulfur. Examples of such monocyclic rings include oxaziridinyl, homopiperazinyl, oxiranyl, dioxiranyl, aziridinyl, pyrrolidinyl, azetidinyl, pyrazolidinyl, oxazolidinyl, piperidinyl, piperazinyl, morpholinyl, thiomorpholinyl, thiazolidinyl, hydantoinyl, valerolactamyl, oxiranyl, oxetanyl, dioxolanyl, dioxanyl, oxathiolanyl, oxathianyl, dithianyl, dihydrofuranyl, tetrahydrofuranyl, dihydropyranyl, tetrahydropyranyl, tetrahydropyridyl, tetrahydropyrimidinyl, tetrahydrothiophenyl, tetrahydrothiopyranyl, diazepanyl, and azepanyl. Examples of such bicyclic rings include indolinyl, isoindolinyl, benzopyranyl, quinuclindinyl, 2,3,4,5-tetrahydro-1,3,benzazepine, 4-(benzo-1,3,dioxol-5-methyl)piperazine, and tetrahydroisoquinolinyl. Further, "substituted heterocyclyl" may refer to a heterocyclyl ring which has additional (e.g. one or more) oxygen atoms bonded to the ring atoms of parent heterocylcyl ring. An example of a heterocyclyl substituted with one or more oxygen atoms is 1,1-dioxido-1,3-thiazolidinyl. The term "alkylthio" as used in this disclosure refers to a divalent sulfur with alkyl occupying one of the valencies and includes the groups methylthio, ethylthio, propylthio, butylthio, pentylthio, hexylthio, and octylthio. The term "alkanoyl" used in this disclosure refers to an alkyl group having 2 to 18 carbon atoms that is bound with a double bond to an oxygen atom. Examples of alkanoyl include, acetyl, propionyl, butyryl, isobutyryl, pivaloyl, valeryl, hexanoyl, octanoyl, lauroyl, and stearoyl. Examples of aroyl are benzoyl and naphthoyl, and "substituted aroyl" may refer to benzoyl or naphthoyl substituted by at least one substituent including those selected from halogen, amino, nitro, hydroxy, alkyl, alkoxy and haloalkyl at the benzene or naphthalene ring. The term "arylalkyl" as used in this disclosure refers to a straight or branched chain alkyl moiety having 1 to 8 carbon atoms that is substituted by an aryl group or a substituted aryl group having 6 to 12 carbon atoms, and includes benzyl, 2-phenethyl, 2-methylbenzyl, 3-methylbenzyl, 4-methylbenzyl, 2,4-dimethylbenzyl, 2-(4-ethylphenyl)ethyl, 3-(3-propylphenyl)propyl. The term "heteroarylcarbonyl" as used in this disclosure refers to a heteroaryl moiety with 5 to 10 membered mono- or fused-heteroaromatic ring having at least one heteroatom selected from nitrogen, oxygen and sulfur as mentioned above, and includes, for example, furoyl, nicotinoyl, isonicotinoyl, pyrazolylcarbonyl, imidazolylcarbonyl, pyrimidinylcarbonyl, and benzimidazolyl-carbonyl. Further, "substituted heteroarylcarbonyl" may refer to the above mentioned heteroarylcarbonyl which is substituted by at least one substituent selected from halogen, amino, vitro, hydroxy, alkoxy and haloalkyl on the heteroaryl nucleus, and includes, for example, 2-oxo-1,3-dioxolan-4-ylmethyl, 2-oxo-1,3-dioxan-5-yl. "Vinyl" refers to an unsaturated substituent having at least one unsaturated double bond and having the formula CH2=CH—. Accordingly, said "substituted vinyl" may refer to the above vinyl substituent having at least one of the protons on the terminal carbon atom replaced with alkyl, cycloalkyl, cycloalkylalkyl, aryl, substituted aryl, heteroaryl or substituted heteroaryl. The term "hydrocarbyl" as used herein refers to a univalent hydrocarbon group containing up to about 24 carbon atoms (i.e. a group containing only carbon and hydrogen atoms) and that is devoid of olefinic and acetylenic unsaturation, and includes alkyl, cycloalkyl, alkyl-substituted cycloalkyl, cycloalkyl-substituted cycloalkyl, cycloalkylalkyl, aryl, alkyl-substituted aryl, cycloalkyl-substituted aryl, arylalkyl, alkyl-substituted aralkyl, and cycloalkyl-substituted aralkyl. Further, functionally-substituted hydrocarbyl groups may refer to a hydrocarbyl group that is substituted by one or more functional groups selected from halogen atoms, amino, nitro, hydroxy, hydrocarbyloxy (including alkoxy, cycloalkyloxy, and aryloxy), hydrocarbylthio (including alkylthio, cycloalkylthio, and arylthio), heteroaryl, substituted heteroaryl, alkanoyl, aroyl, substituted aroyl, heteroarylcarbonyl, and substituted heteroarylcarbonyl.

Another exemplified embodiment of the invention is shown by Formula (3) below which is also known as Complex 1. In this embodiment, A and B in Formula (1) are phenyl rings which are substituted at each cis position with isopropyl, and R6 and R7 are hydrogen and [anion] is hexaflurophosphate:

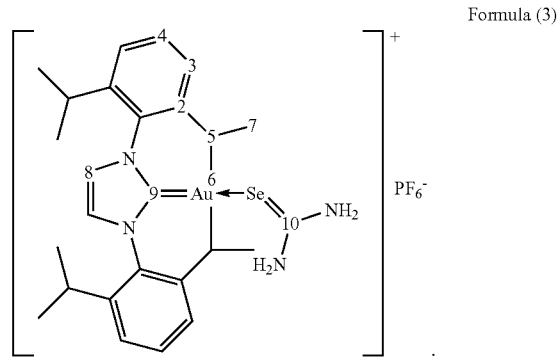

Formula (3)

This complex contains both a carbine and selenourea as ligands for gold. The [NHC-Au] component of Complex (1) stabilizes Au(1) under physiological conditions thus preventing oxidation of Au(1) to Au(III) or its reduction to Au(0) thus preserving biological activity of the Au(I) carbine complex.

The complex of Formula (3) has also been found to be stable in polar solvents such as water, methanol, ethanol and acetone, as well as in deuterated solvents such a dichloromethane. The inventors found that when the complex of Formula (3) was formed by adding 1 eq. of selenourea to 0.5 to 1.0 eq. of NHC-Au—Cl, that only one cationic product was formed: that identified by Formula (3). In contrast, similar methods for making related compounds often produce a mixture of products which have different structures and chemical or physical properties.

The term active ingredient, as used herein, refers to an ingredient in the composition that is biologically active, for example the gold(I) carbene complexes disclosed herein, salt thereof, a prodrug thereof, or a solvate thereof is active against cancer or tumor cells.

Compositions.

In many embodiments, the gold(I) carbene complex of the invention, the salt thereof, the solvate thereof, the prodrug thereof, or the combination thereof is formulated in a pharmaceutically acceptable composition. As used herein, a "composition" refers to a mixture of the active ingredient with other chemical components, such as pharmaceutically acceptable carriers and excipients. One purpose of a composition is to facilitate administration of the gold(I) carbine complex of the invention, the salt thereof, the solvate thereof, the prodrug thereof, or a combination thereof to a subject. Depending on the intended mode of administration (oral, parenteral, or topical), the composition can be in the form of solid, semi-solid or liquid dosage forms, such as tablets, suppositories, pills, capsules, powders, liquids, or suspensions, preferably in unit dosage form suitable for single administration of a precise dosage. The phrase "pharmaceutically acceptable" as used herein refers to compounds, counterions, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. Therefore, the composition refers to the combination of an active ingredient with a carrier, inert or active, making the composition especially suitable for diagnostic or therapeutic use in vivo, ex viva, or in vitro.

As used herein, a pharmaceutically acceptable carrier refers to a carrier or diluent that does not cause significant irritation to an organism, does not abrogate the biological activity and properties of the administered active ingredient, and/or does not interact in a deleterious manner with the other components of the composition in which it is contained. The term "carrier" encompasses any excipient, binder, diluent, filler, salt, buffer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in *Remington's Pharmaceutical Sciences,* 21st Edition, ed. University of the Sciences in Philadelphia, Lippincott, Williams & Wilkins, Philadelphia Pa., 2005, which is incorporated herein by reference in its entirety. Examples of physiologically acceptable carriers include buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN® (ICI, Inc.; Bridgewater, N.J.), polyethylene glycol (PEG), and PLURONICS® (BASF Florham Park, N.J.). An "excipient" refers to an inert substance added to composition to further facilitate administration of a compound. Examples, without limitation, of excipients include calcium carbonate, calcium phosphate, various sugars and types of starch, cellulose derivatives, gelatin, vegetable oils, and polyethylene glycols.

In other embodiments, the composition has various release rates (e.g., controlled release or immediate release). Immediate release refers to the release of an active ingredient substantially immediately upon administration. In another embodiment, immediate release occurs when there is dissolution of an active ingredient within 1-20 minutes after administration. Dissolution can be of all or less than all (e.g. about 70%, about 75%, about 80%, about 85%, about 90%, about 91%, about 92%, about 93%, about 94%, about 95%, about 96%, about 97%, about 98%, about 99%, about 99.5%, 99.9%, or 99.99%) of the active ingredient. In another embodiment, immediate release results in complete or less than complete dissolution within about 1 hour following administration. Dissolution can be in a subject's stomach and/or intestine. In one embodiment, immediate release results in dissolution of an active ingredient within 1-20 minutes after entering the stomach. For example, dissolution of 100% of an active ingredient can occur in the prescribed time. In another embodiment, immediate release results in complete or less than complete dissolution within about 1 hour following rectal administration. In some embodiments, immediate release is through inhalation, such that dissolution occurs in a subject's lungs.

Controlled-release or sustained-release refers to the release of an a iveingredient from a composition or dosage form in which the active ingredient is released over an extended period of time. In one embodiment, controlled-release results in dissolution of an active inuredient within 20-180 minutes after entering the stomach. In another embodiment, controlled-release occurs when there is dissolutton of an active edient ithin 20-180 minutes after swallowed. In another embodiment, controlled-release occurs when there is dissolution of an active ingredient within 20-180 minutes after entering the intestine. In another embodiment, controlled-release results in substantially complete dissolution after at least 1 hour following administration. In another embodiment, controlled-release results in substantially complete dissolution after at least 1 hour following oral administration. In another embodiment, controlled-release results in substantially complete dissolution after at least 1 hour following rectal administration. In another embodiment, controlled-release results in substantially complete release of the active Au(I) complex after or over at least 1, 2, 4, 8, 12, 24 hours or 2, 3, 4, 5, 6, or 7 days (or any intermediate value within this range) following administration including a depot administration into or around a tumor. In one embodiment, the composition is not a controlled-release composition.

Solid dosage forms for oral administration can include capsules, tablets, pills, powders, and granules. In such solid dosage forms, the active ingredient is ordinarily combined with one or more adjuvants appropriate to the indicated route of administration. If administered per os, the active ingredient can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering ingredients such as sodium citrate, magnesium or calcium carbonate or bicarbonate. Tablets and pills can additionally be prepared with enteric coatings.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting ingredients, emulsifying and suspending ingredients, and sweetening, flavoring, and perfuming ingredients.

For therapeutic purposes, formulations for parenteral administration can be in the form of aqueous or non-aqueous isotonic sterile injection solutions or suspensions. The term "parenteral", as used herein, includes intravenous, intravesical, intraperitoneal, subcutaneous, intramuscular, intralesional, intracranial, intrapulmonal, intracardial, intrasternal, and sublingual injections, or infusion techniques. These solutions and suspensions can be prepared from sterile powders or granules having one or more of the carriers or diluents mentioned for use in the formulations for oral administration. The active ingredient can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Injectable preparations, for example, sterile injectable aqueous or oleaginous suspensions can be formulated according to the known art using suitable dispersing or wetting ingredients and suspending ingredients. The sterile injectable preparation can also be a sterile injectable solution or suspension in a non-toxic parenterally acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or diglycerides. In addition, fatty acids, such as oleic acid, find use in the preparation of injectables. Dimethyl acetamide, surfactants including ionic and non-ionic detergents, polyethylene glycols can be used. Mixtures of solvents and wetting ingredients such as those discussed above are also useful.

Suppositories for rectal administration can be prepared by mixing the active ingredient with a suitable non-irritating excipient, such as cocoa butter, synthetic mono-, di-, or triglycerides, fatty acids, and polyethylene glycols that are solid at ordinary temperatures but liquid at the rectal temperature and will therefore melt in the rectum and release the drug.

Topical administration can also involve the use of transdermal administration such as transdermal patches or iontophoresis devices. Formulation of drugs is discussed in, for example, Gernnaro *Remington's Pharmaceutical Sciences*, 18$^{th}$ edition, 1990 or by Nems, et al., *Pharmaceutical Dosage Forms: Parenetral Medications*, Third Edition (2010) which are both incorporated herein by reference).

Other active ingredients. The terms active ingredient or other active ingredient, as used herein, refers to an ingredient in the composition that is biologically active, for example, the gold(I) complexes disclosed herein, a salt thereof, a prodrug thereof, or a solvate thereof. Other active ingredients include, but are not limited to, those that exert a substantial pharmacokinetic or pharmacodynamic activity when in admixture with a gold(I) complex, for example, other anti-cancer drugs, immunopotentiators, or other agents. In some embodiments, other active ingredients in addition to the gold(I) complex may be incorporated into a composition or separately administered in conjunction with a gold(I) complex. In one embodiment, the composition is used for treating cancer and further comprises a second active ingredient, such as a chemotherapeutic or immunotherapeutic agent, for the treatment or prevention of neoplasm, of tumor or cancer cell division, growth, proliferation and/or metastasis in the subject induction of death or apoptosis of tumor and/or cancer cells; and/or any other form of proliferative disorder. Exemplary chemotherapeutic agents include, without limitation, aflibercept, asparaginase, bleomycin, busulfan, carmustine, chlorambucil, cladribine, cyclophosphamide, cytarabine, dacarbazine, daunorubicin, doxonibicin, etoposide, fludarabine, gemcitabine, hydroxyurea, idarubicin, ifosfamide, irinotecan, lomustine, mechlorethamine, melphalan, mercaptopurine, methotrexate, mitomycin, mitoxantrone, pentostatin, procarbazine, topotecan, vinblastine, vincristine, retinoic acid, oxaliplatin, carboplatin, 5-fluorouracil, teniposide, amasacrine, docetaxel, paclitaxel, vinorelbine, bortezomib, clofarabine, capecitabine, actinomycin D, epirubicin, vindesine, methotrexate, 6-thioguanine, tipifarnib, imatinib, erlotinib, sorafenib, sunitibib, dasatinib, nilotinib, lapatinib, gefitinib, temsirolimus, everolimus, rapamycin, bosutinib, pzopanib, axitinib, neratinib, vatalanib, pazopanib, midostaurin, enzastaurin, trastuzumab, cetuximab, panitumumab, rituximab, bevacizumab, mapatumumab, conatumumab, and lexatumumab. The composition may comprise 0.1-99 wt % of the second active ingredient, preferably 10-50 wt %, more preferably 10-20 wt % relative to the weight of the first active ingredient. These ranges include all intermediate values. Alternatively, an amount of an additional active ingredient may substantially be its of dose, which when combined with gold(I) complex of the invention may be reduced by 5, 10, 15, 20, 25, 30, 35, 40, 45, 50, 55, 60, 65, 70, 75, 80, 85, 90 or 95% to obtain substantially the same effect as higher dosages of either the gold(I) complex or the additional active ingredient, thus reducing toxicity associated with administration of a higher dose of either ingredient.

Anticancer properties of a compound or composition ay be evaluated by methods known in the art, including these described by and incorporated by reference to Y. F. To, et al., Int. J. Cancer, 2009, 124, 1971-1979; C. T. Lum, et al., Int. J. Cancer, 2006, 118, 1527-1538: C. T. Lum, et al., Chem. Commun., 2013, 49, 4364-4366; C.-M. Che, et al., Chem. Commun., 2003, 1718-1719; Y. Wang, et al., Eur. J. Pharmacol., 2007, 554, 113-122 each incorporated by reference.

In some embodiments, the Au(I) complexes of the invention exhibit anti-cancer activity against cancer cells that are or have become resistant to conventional anti-cancer drugs such as cisplatin. When resistance develops to a conventional anticancer drug, treatment y be continued with a gold(I) complex of the invention to which the cancer cells are sensitive.

Cytotoxic Activity.

In one embodiment, the IC$_{50}$ of the gold(I) complexes is in a range of 0.01-200 µM, 0.1-100 µM, 1-100 µM, 10-90 µM, 20-80 µM, 30-80 µM, 40-80 µM, 50-80 µM, or 50-75 µM. These ranges include all intermediate subranges and values.

As used herein, the term "IC$_{50}$" refers to a concentration of a gold(I) complex, the salt thereof, the prodrug thereof, or the solvate thereof, which causes the death of 50% of cancer or proliferating cells in 72 hours (3 days) such as the MCF-7, A2780, A2780R, or 22Rv1 cancer cell lines described herein. The IC$_{50}$ can be determined by standard cell viability assays, such as, without limitation, ATP test, calcein AM assay, clonogenic assay, ethidium homodimer assay, Evans blue assay, Fluorescein diacetate hydrolysis/propidium iodide staining assay, flow cytometry assay, formazan-based assays (MTT, XTT), green fluorescent protein assay, lacate dehydrogenase assay, methyl violet assay, propidium iodide assay, Resazurin assay, Trypan Blue assay and TUNEL assay. Preferably, a MTT assay and/or a Trypan Blue assay is used.

Biomarkers.

Alternatively to use of $IC_{50}$ values, efficacy of treatment with a gold(I) complex of the invention may be determined by measuring or detecting a change in one or cancer biomarkers, for example, comparing quantity of biomarkers in a blood or tissue sample before and after a treatment.

A treatment may significantly decrease the concentration of a particular biomarker, for example, by 5, 10, 15, 20, 25, 30, 35, 40, 45, 50, 55, 60, 65, 70, 75, 80, 85, 90, or 100%, compared to a control or pre-treatment value. As used herein, the term "biomarker" refers to a characteristic that is objectively measured and evaluated as an indicator of normal biological processes, pathogenic processes or pharmacological responses to a therapeutic intervention. Biomarkers include ER/PR, HER-2/neu for breast cancer, EGFR, KRAS, UGT1A1 for colorectal cancer, EML4/ALK, EGFR, and KRAS for lung cancer as well as other biomarkers described and incorporated by reference to en.wikipedia.org/wiki/Cancer_biomarkers (last accessed Oct. 5, 2017). Cancer biomarkets are useful in determining the aggressiveness of an identified cancer as well as its likelihood of responding to the treatment. Examples of such prognostic biomarkers include, without limitation, CA125, β2-microglobulin, and EBV DNA. A change or mutation in a biomarker may be detected with a polymerase chain reaction (PCR) assay, DNA microarray, multiplex ligation-dependent probe amplification (MLPA), single strand conformational polymorphism (SSCP), denaturing gradient gel electrophoresis (DCGGE), heteroduplex analysis, and restriction fragment length polymorphism (RFLP). The procedures to detect the mutation are well-known to those of ordinary skill in the art. The concentration of the biomarker may be measured with an assay, for example an antibody-based method (e,g., an ELISA). As used herein, the term antibody-based method refers to any method with the use of an antibody including, but not limited to, enzyme-linked immunosorbent assay (ELISA), Western blotting, immunoprecipitation (IP), enzyme linked immonospot (ELISPOT), immunostaining, immunohistochemistry, immunocytochemistry, affinity chromatography, and the like. Preferably, an ELISA is used. The term ELISA refers to a method of detecting the presence and concentration of a biomarker in a sample, for example, before, during or after treatment with a gold(I) selenone complex of the invention. There are several variants of ELISA, including, but not limited to, sandwich ELISA, competitive ELISA, indirect ELISA, ELISA reverse, and the like. The ELISA assay may be a singleplex assay or a multiplex assay, which refers to a type of assay that simultaneously measures multiple analytes in a single run/cycle of the assay. Preferably, a sandwich ELISA is used. The protocol for measuring the concentration of the biomarker and/or detecting the mutation in the biomarker is known to those of ordinary skill, for example by performing the steps outlined in the commercially available assay kit sold by Sigma-Aldrich, Thermo Fisher Scientific, R & D Systems ZeptoMetrix Inc., Cayman Inc., Abcam, Trevigen, Dojindo Molecular Technologies, Biovision, and Enzo Life Sciences. The term sample includes any biological sample taken from the subject including a cell, tissue sample, or body fluid. For example, a sample may include a tumor sample, skin sample, a cheek cell sample, saliva, or blood cells. A sample can include, without limitation, a single cell, multiple cells, fragments of cells, an aliquot of a body fluid, whole blood, platelets, serum, plasma, red blood cells, white blood cells, endothelial cells, tissue biopsies, synovial fluid, and lymphatic fluid. In some embodiments, the sample is taken from a tumor. In some embodiments, the concentration of the biomarker is measured before and after the administration. When the concentration of the biomarker is maintained, the method may further comprise increasing the effective amount of at least one of the gold(I) complex of the invention, the salt thereof, the solvate thereof, the prodrug thereof, and the combination thereof by at least 5%, at least 10%, or at least 30%, up to 50%, up to 60%, or up to 80% of an initial effectiveamount that is in a range of 1-100 mg/kg based on the weight of the subject. The subject may be administered with the increased dosage for a longer period (e.g., 1 week more, 2 weeks more, or 2 months more) than the duration with the initial effective amount. In some embodiments, the mutation in the biomarker is detected before administrating the composition to identify subjects predisposed to the disease. For example, women with a BRCA1 germline mutation are at a higher risk of contracting ovarian cancer. In some embodiments, the biomarkers are measured/detected after each administration. For example, the measurement may be 1-5 minutes, 1-30 minutes, 30-60 minutes, 1-2 hours, 2-12 hours, 12-24 hours, 1-2 days, 1-15 weeks, 15-20 weeks, 20-30 weeks, 30-40 weeks, 40-50 weeks, 1 year, 2 years, or any period of between after the administration.

Subjects.

The terms "patient", "subject", and "individual" are used interchangeably. As used herein, they refer to individuals suffering from a disease, at risk of further progression of a disease, or at risk of acquiring or developing the disease. None of these terms require that the individual be under the care and/or supervision of a medical professional.

These terms generally refer to humans, but also apply to mammals, avians and other animals, especially domesticated or ecologically or commercially valuable animals. Mammals include non-human primates, such as chimpanzees, and other apes and monkey species, farm animals, such as cattle, horses, sheep, goats, swine, domestic animals, such as rabbits, dogs, and cats, laboratory animals including rodents, such as rats, mice and guinea pigs, and the like. In a preferred embodiment, the subject is a human.

A subject in need of treatment includes a subject already with a disease such as cancer, a subject who does not yet experience or exhibit symptoms of the disease, and a subject who is predisposed to the disease for example based on family history or genetic profile. In preferred embodiments, the subject is a person who is predisposed to cancer such as a person with a family history of cancer. In another embodiment, the subject refers to a cancer patient who has been previously administered/treated with cisplatin and have cisplatin resistance, for example in the form of high ERCC1 mRNA levels, overexpression of HER-2/neu, activation of the PI3-K/Akt pathway, loss of p53 function, and/or overexpression of antiapoptotic bcl-2). Subjects at risk of, or infected with a microorganism, such as a gram-positive or gram-negative bacterium, yeast, fungus, or parasite sensitive to a gold(I) complex of the invention are also included in those who would benefit from prophylaxis or treatment.

Cancers/Proliferative Disorders.

Cancers such as, but not limited to, sarcomas, carcinomas, melanomas, myelomas, gliomas and lymphoma (including Hodkin lymphoma), can be prevented or treated with the Au(I) complexes provided herein.

A cancer may be staged using the TNM system, described and incorporated by reference to text available at www.cancer.gov/about-cancer/diganosis-staging/staging (last accessed Oct. 9, 2017). In some embodiments, a gold(I) complex of the invention will be administered to a subject having a Stage 0, I, II, III, or IV cancer. At stage 0 abnormal cells are present but have not spread to nearby tissue (carcinoma in situ). At Stages I, II and III, cancer is present with a higher stage number being associated with larger tumor burden and broader spread, At Stage IV, the cancer has spread to distant parts of the body.

In some embodiments, methods incorporating the use a gold(I) complex of the present disclosure to treat or prevent cancer of the blood, brain, bladder, lung, cervix, ovary, colon, rectum, pancreas, skin, prostate gland, stomach, breast, liver, spleen, kidney, head, neck, testicle, bone, bone marrow, thyroid gland or central nervous system. In some embodiments, these methods are effective in the treatment or prevention of cervical, colon, prostate, and lung cancers.

Cancers or tumor resistant to other anticancer drugs, such as cisplatin-resistant cancers, may be treated. In treating certain cancers, the best approach is often a combination of surgery, radiotherapy, and/or chemotherapy. Therefore, in at least one embodiment, the composition is employed in conjunction with conventional radiotherapy and/or chemotherapy. In another embodiment, the composition is employed with surgery. The radiotherapy and/or surgery may be before or after the composition is administered.

Other non-cancerous proliferative diseases, disorders or conditions may also be treated, such as atherosclerosis, rheumatoid arthritis, psoriasis, idiopathic pulmonary fibrosis, scleroderma, cirrhosis of the liver, or benign proliferative conditions such as verruca (warts), dermatitis, or other disorders characterized by epidermal cell proliferation.

Breast cancer is cancer that develops from breast tissue. Signs of breast cancer may include a lump in the breast, a change in breast shape, dimpling of the skin, fluid coming from the nipple, or a red scaly patch of skin. In breast cancers with distant spread of the disease, there may be bone pain, swollen lymph nodes, shortness of breath, or yellow skin. Risk factors for developing breast cancer include being female, obesity, lack of physical exercise, drinking alcohol, her none replacement therapy during menopause, ionizing radiation, early age at first menstruation, having children late or not at all, older age, and family history. About 5-10% of cases are due to genes inherited from a person's parents, including BRCA1 and BRCA2 among others. The gold(I) complex of the invention may be administered by itself or in combination with other therapy to a subject at risk of breast cancer, a subject diagnosed with breast cancer, or a subject under treatment for breast cancer, or a subject who has already been treated for breast cancer, for example, by removal of breast tissue.

Colon cancer, bowel cancer, or colorectal cancer develops and manifests in the colon and rectum which are parts of the large intestine. Colon cancers represent abnormal growth of cells that have the ability to invade or spread to other parts of the body. Signs and symptoms may include blood in the stool, a change in bowel movements, weight loss, and feeling tired all the time. Most colorectal cancers are associated with old age and can occur in subjects 50, 55, 60, 80 or more years of age. Colon cancer is also associated with lifestyle factors and some cases are associated genetic risks. Risk factors include diet, obesity, smoking, and lack of physical activity. Dietary factors that increase the risk include red and processed meat as well as alcohol. Another risk factor is inflammatory bowel disease, which includes Crohn's disease ulcerative colitis. Some of the inherited genetic disorders that can cause colorectal cancer include familial adenomatous polyposis and hereditary non-polyposis colon cancer. Colon cancer often starts as a benign tumor, often in the form of a polyp, which over time becomes cancerous. The most common metastasis sites for colorectal cancer are the liver, the lung and the peritoneum. Treatments used for colorectal cancer may often include a combination of surgery, radiation therapy, chemotherapy and targeted therapy.

Lung cancer of lung carcinoma is a malignant lung tumor characterized by uncontrolled cell growth in tissues of the lung and can metatasize to nearby and distant tissues. Most cancers that start in the lung, known as primary lung cancers, are carcinomas and the two main types are small-cell lung carcinoma (SCLC) and non-small-cell lung carcinoma (NSCLC). The most common symptoms are coughing (including coughing up blood), weight loss shortness of breath, and chest pains. The vast majority (85%) of cases of lung cancer are due to long-term tobacco smoking, however some cases are associated with or caused by combination of genetic factors and exposure to environmental factors such as radon gas, asbestos, second-hand smoke, or other forms of air pollution. Lung cancer may be seen on chest radiographs and computed tomography (CT) scans and diagnosis is usually confirmed by biopsy which is usually performed by bronchoscopy or CT-guidance. Common treatments include surgery, chemotherapy, and radiotherapy. NSCLC is sometimes treated with surgery, whereas SCLC usually responds better to chemotherapy and radiotherapy.

Therapy.

As used herein, the terms "therapies" and "therapy" can refer to any method, composition, and/or active ingredient that can be used in the treatment and/or management of the disease or one or more symptoms thereof. In some embodiments, the method for treating the disease involves the administration of a unit dosage or a therapeutically effective amount of the active ingredient to a subject in need thereof. A subject may be selected for treatment based on known risk factors or by diagnosis.

Administration.

The terms "administer", "administering", "administration", and the like, as used herein, refer to the methods that may be used to enable delivery of the active ingredient and/or the composition to the desired site of biological action. Routes or modes of administration are as set forth herein. These methods include, but are not limited to, oral routes, intraduodenal routes, parenteral injection including intravenous, subcutaneous, intraperitoneal, intramuscular, intravascular, or infusion, topical and rectal administration. Those of ordinary skill in the art are familiar with administration techniques that can be employed with the compounds and methods described herein. In preferred embodiments, the active ingredient and/or the composition described herein are administered orally.

The terms effective amount, therapeutically effective amount, or "pharmaceutically effective amount refer to that amount of the active ingredient being administered which will relieve to some extent one or more of the symptoms of the disease being treated. The result can be reduction and/or alleviation of the signs, symptoms, or causes of a disease, or any other desired alteration of a biological system. For example, an "effective amount" for therapeutic uses is the amount of the gold(I) complex of the invention, the salt thereof, the solvate thereof, the prodrug thereof, or a combination thereof as disclosed herein required to provide a clinically significant decrease in a disease. An appropriate "effective amount" may differ from one individual to another. An appropriate "effective amount" in any individual case may be determined using techniques, such as a dose escalation study.

The dosage and treatment duration are dependent on factors, such as bioavailability of a drug, administration mode, toxicity of a drug, gender, age, lifestyle, body weight, the use of other drugs and dietary supplements, the disease stage, or tolerance and resistance of the body to the administered drug, and then determined and adjusted accordingly. In at least one embodiment, the at least one of the gold(I) complex of the invention, the salt thereof, the solvate thereof, the prodrug thereof, and the combination thereof is administered in an effective amount in a range of 1-100 mg/kg based on the weight of the subject, preferably 10-80 mg/kg, more preferably 20-50 mg/kg.

In some embodiments, a treatment will involve administering a composition comprising at least 0.01, 0.05, 0.1, 0.5 wt %, 5 wt %, 10 wt %, 15 wt %, 20 wt %, 25 wt %, 30 wt %, 35 wt %, 40 wt %, 45 wt %, 50 wt %, 55 wt %, 60 wt %, 65 wt %, 70 wt %, 75 wt %, 80 wt %, 85 wt %, 90 wt %, 95 wt %, 99 wt %, or 99.9 wt %, of the gold(I) complex of the invention. The composition may comprise 0.01-50 μM, 0.01-30 μM, preferably 0.01-10 μM of the gold(I) complex of the theinvention relative to the total composition. In some embodiments, the composition comprises up to 0.1 wt %, 1 wt %, 5 wt %, or 10 wt % of the pharmaceutically acceptable salt of the gold(I) complex of the invention. In some embodiments, the composition comprises up to 0.1 wt %, 1 wt %, 5 wt %, or 10 wt % of the pharmaceutically acceptable solvate thereof of either the gold(I) complex of the invention. These ranges include all intermediate subranges and values.

A treatment method may comprise administering a composition containing the gold(I) complex of the invention as a single dose or multiple individual divided doses. In some embodiments, the composition is administered at various dosages (e.g., a first dose with an effective amount of 50 mg/kg and a second dose with an effective amount of 10 mg/kg). In some embodiments, the interval of time between the administration of the composition and the administration of one or more additional therapies may be about 1-5 minutes 1-30 minutes, 30 minutes to 60 minutes, 1 hour, 1-2 hours, 2-6 hours, 2-12 hours, 12-24 hours, 1-2 days, 2 days, 3 days, 4 days, 5 days, 6 days, 7 days, 1 week, 2 weeks, 3 weeks, 4 weeks, 5 weeks, 6 weeks, 7 weeks, 8 weeks, 9 weeks, 10 weeks, 15 weeks, 20 weeks, 26 weeks, 52 weeks, 11-15 weeks, 15-20 weeks, 20-30 weeks, 30-40 weeks, 40-50 weeks, 1 month, 2 months, 3 months, 4 months, 5 months, 6 months, 7 months, 8 months, 9 months, 10 months, 11 months, 12 months, 1 year, 2 years, or any period of time in between. Preferably, the composition is administered once daily for at least 2 days, 5 days, 6 days, or 7 days. In certain embodiments, the composition and one or more additional therapies are administered less than 1 day, 1 week, 2 weeks, 3 weeks, 4 weeks, one month, 2 months, 3 months, 6 months, 1 year, 2 years, or 5 years apart.

EMBODIMENTS

The following examples illustrate various aspects of the present invention. They are not to be construed to limit the embodiments in any manner whatsoever.

1. A method for treating a proliferative disease, disorder or condition in a subject, comprising:
   administering to a subject in need thereof a complex according to Formula (I).

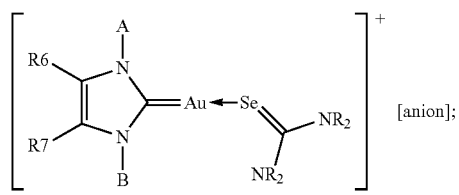

wherein A and B are, independently, selected from the group of unsubstituted or substituted 5, 6, 7 or 8-membered rings,
wherein R6 and R7 are, independently, hydrogen, $C_1$-$C_6$ alkyl, —OH, or —OR; and
wherein each $R_2$ is independently, hydrogen, $C_1$-$C_6$ alkyl, or a bond; and
wherein the two $NR_2$ groups may together with two or more intervening carbon or heteroatoms form a 5, 6, 7 or 8-membered ring.

2. The method of embodiment 1, wherein R6 and R7 are hydrogen,
3. The method of embodiment 1, wherein A and B are, independently, phenyl that is substituted in the 2 and 6 positions with at least one of hydrogen, alkyl, or aryl.
4. The method of embodiment 1, wherein A and B are phenyl substituted at the 2 and 6 positions with isopropyl.
5. The method of embodiment 1, wherein each R2 is, independently, hydrogen or C1-C6 alkyl.
6. The method of embodiment 1, wherein the two R2 groups form a 5, 6, 7 or 8-membered ring.
7. The method of embodiment 1, wherein the anion is $PF_6$.
8. The method of embodiment 1, wherein the complex is [Au(Ipr)(Seu)]$PF_6$ (1), wherein Ipr is 1,3-bis(2,6-diisopropylphenyl)imidazol-2-ylidene, Seu is selenourea, and the anion is $PF_6$.
9. The method of embodiment 1, wherein the proliferative disease, disorder or condition is cancer.
10. The method of embodiment 1, wherein the proliferative disease, disorder, or condition is breast cancer.
11. The method of embodiment 1, wherein the proliferative disease, disorder, or condition is colon cancer.
12. The method of embodiment 1, wherein the proliferative disease, disorder, or condition is lung cancer.
13. A complex according to Formula (I):

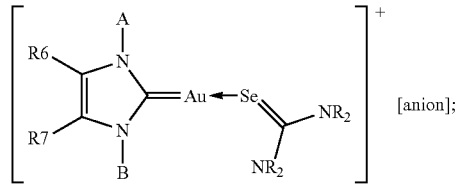

wherein A and B are, independently, selected from the group of unsubstituted or substituted 5, 6, 7 or 8-membered rings,
wherein R6 and R7 are, independently, hydrogen, $C_1$-$C_6$ alkyl, —OH, or —OR; and
wherein each $R_2$ is independently hydrogen, $C_1$-$C_6$ alkyl, or a bond; and
wherein they two $NR_2$ groups may together with two or more intervening carbon or heteroatoms form a 5, 6, 7 or 8-membered ring.

14. The complex of embodiment 13, wherein R6 and R7 are hydrogen.
15. The complex of embodiment 13, wherein A and B are, independently, phenyl that is substituted in the 2 and 6 positions with at least one of hydrogen, alkyl, or aryl.
16. The complex of emmbodiment 13, wherein each $R_2$ is, independently, hydrogen or C1-C6 alkyl.
17. The complex of embodiment 13 wherein the two $R_2$ groups form a 5, 6, or 8-membered ring.
18. The complex of embodiment 13, wherein the anion is $PF_6$.
19. The complex of embodiment 13, wherein the complex is [Au(Ipr)(Seu)]$PF_6$ (1), wherein Ipr is 1,3-bis-(2,6-di-isopropylphenyl)imidazol-2-ylidene, Seu is selenourea, and the anion is $PF_6$.
20. A pharmaceutical composition comprising at least one gold(I) complex of embodiment 13 in combination with at least one pharmaceutically acceptable carrier or excipient and, optionally, at least one other anticancer drug, chemotherapeutic agent, or immunopotentiator.

EXAMPLES

The examples below are intended to further illustrate protocols for assessing the methods and compounds described herein, and are not intended to limit the scope of the claims.

Example 1

Gold(I)-carbene complex (1) so designated [Au(IPr)(Seu)]$PF_6$ (where Seu=Selenourea and IPr=1,3-Bis(2,6-diisopropylphenyl) imidazol-2-ylidene) was prepared by mixing a solution of 0.127 g (0.500 mmol) Ag$Pf_6$ in 5 mL ethanol and 0.311 g (0.500 mmol) chlorido[1,3-Bis(2,6-di isopropylphenyl)imidazol-2-ylidene]gold(I), [Au(Ipr)(Cl)] (both obtained from Sigma-Aldrich) in 5 mL $CH_2Cl_2$. After stirring for 5 min at room temperature, the solution was filtered. To the filtrate, 0.0615 g (0.500 mmol) Seu was added. The solution was stirred for 1 hour and filtered. After three days colorless crystals were obtained from the filtrate. Yield=75%. Analysis: Calculated for $C_{28}H_{40}AuF_6N_4PSe$; C, 39.60; H, 4.72; N, 5.56. Found: C, 40.04; H, 5.23; N, 6.04. Melting point=195-98° C.

The solid state FTIR spectra were recorded on a Perkin-Elmer FTIR 180 spectrophotometer using KBr pellets over the range 4,000-400 cm$^{-1}$. The solution $^1H$, $^{13}C$ and $^{77}Se$ NMR spectra in CDCl$_3$ were recorded on a LAMBDA LA-500 NMR spectrophotometer operating at the frequencies of 500.01, 125.65 and 200.0 MHz respectively. The spectral conditions for $^{13}C$ NMR were: 32 k data points, 0.967 s acquisition time, and 1.00 s pulse delay and 45° pulse angle. The $^{77}Se$ NMR chemical shifts were recorded relative to an external reference (NaHSeO$_3$ in D$_2$O) at 1308.00 ppm, using a 2.00 s pulse delay and 0.311 s acquisition time. The X-ray data of 1 was collected at 173K on a STOE IPSD II Image Plate Diffraction System connected with a two-circle goniometer and using MoKα graphite monochromator (λ=0.71.073 Å). The structure was solved by SHELXS-2014 program. See G. M. Sheldrick, A short of SHELX, Acta Cryst. A64, 112-122, 2008, incorporated herein by reference in its entirety. The refinement and further calculations were carried out with SHELXL-2014. See G. M. Sheldrick, Crystal Refinement with SHELXL, Acta Cryst. C71 (2015) 3-8, incorporated herein by reference in its entirety. The N—H H atoms were located in a Difference Fourier map and refined with a distance restraint of N—H=0.88(2) Å and H . . . H=1.40(2) Å. The C-bound H-atoms were included in calculated positions and treated as riding atoms: C—H=0.95-1.0 Å with $U_{iso}(H)=1.5U_{eq}(C)$ for methyl H atoms and $=1.21U_{eq}(C)$ for other H-atoms. The non-H atoms were refined anisotropically using weighted full-matrix least squares on F$^2$. A semi-empirical absorption correction was applied using the MULscanABS routine in. PLATON. See A. L. Spek, Structure validation in chemical crystallography, Acta Cryst. D65, 148-155, 2009, incorporated herein by reference in its entirety. The F atoms of the $PF_6^-$ anion are disordered. The best solution was found by distributing the electron density over a total of 11 positions, which were refined with various fixed occupancy ratios to give a total of six F atoms. A summary of crystal data and structure refinement is given in reference [36].

The complexes, [Au(IPr)Cl] and [Au(IPr)(Seu)]$PF_6$ (1) were tested for their in vitro cytotoxic effects against human cell lines; MCF7 (breast cancer), HCl15 (colon cancer) and A549 (lung carcinoma) as reported previously. See M. Altaf, M. Monim-ul-Mehboob, A. A. A. Seliman, A. A. Tsai), V. Dhuna, G. Bhatia, K. Dhuna, Synthesis, X-ray Structures, Spectroscopic Analysis and Anticancer Activity of Novel Gold(I) Carbene Complexes, J. Organomet. Chem, 765 (2014) 68-79, incorporated herein by reference in its entirety. The cells were seeded at the concentration of 3×10$^3$ cells/well in 100 µL of DMEM containing 10% fetal bovine serum (FBS) in a 96-well tissue culture plate and incubated for 72 h at 37° C., 5% CO$_2$ and 90% relative humidity in a CO$_2$ incubator. After that 100 µL of 100, 50, 25 and 12.5 µM solutions of cisplatin and gold(I) complexes prepared in DMEM were added to the cells and the cultures were incubated for 72 h. The medium in the wells was cast off and 100 µL of DMEM containing MTT (0.5 mg/ml) was added to the wells, with subsequent incubation in the CO$_2$ incubator at 37° C. in the dark for 4 h. After incubation, purple-colored formazan produced by the cells appeared as dark crystals in the bottom of the wells. The culture medium was carefully removed from each well to prevent disruption of the monolayer and 100 µL of dimethylsulfoxide (DMSO) was added to each well. The solution in the wells was thoroughly mixed to dissolve the formazan crystals which produce a purple solution. The absorbance of the 96 well-plates was measured at 570 nm with LabSystems Multiskan EX-ELISA reader against a reagent blank. The experimental results are calculated as the micromolar concentration of 50% cell growth inhibition (IC$_{50}$) of each drug. The MTT assay was carried out in three independent experiments for each analysis.

Electrochemical (Square wave stripping voltammetry, SWSV) measurements were performed on a CH Instrument (CHI 1232A) potentiostat. Electrochemical cell comprises of a platinum wire as a counter electrode, an Ag/AgCl saturated with KCl as reference electrode and glassy carbon electrode (GCE; 3.0 mm diameter, Model CHI104, CH Instruments, Austin, Tex.) as a working electrode inserted into 2.0 mL glass cell containing phosphate buffer solution, pH 7.0 as supporting electrolyte. 0.1 M buffer solution was prepared by mixing, appropriate volumes of 0.2 M monosodium phosphate and disodium phosphate prepared with distilled water. Stock solutions of the complex prepared with methanol, while L-tyrosine and L-tryptophan were prepared by dissolving in 0.10 M NaOH in ratio 1:4 with distilled water. GCE was polished with 0.05 µm alumina, rinsed with distilled water prior to every SWSV measurements at room temperature in a quiescent condition at potential windows between −0.20 V and 1.20 V for the stability and 0.00 V and 1.20 V for the interaction studies. Working conditions are; pulse width (increment) 4 mV, pulse height (amplitude) 25 mV and frequency, 15 Hz.

In the IR spectrum of Complex (1) the band at 606 cm$^{-1}$ is assigned to C=Se stretching vibration, which is significantly red-shifted with respect to its position in free Seu (736 cm$^{-1}$). This shift indicates a decrease in the double bond character of C=Se bond upon coordination. The N—H stretching shows a shift to higher frequency region (3468, 3363 Vs 3453, 3265 cm$^{-1}$ for free Seu). The N—H bending vibration of Seu in Complex (1) was detected at 1546 cm$^{-1}$. Weak signals at 2960 & 3073 cm$^{-1}$ for [Au(IPr)Cl] and 2960 & 3160 cm$^{-1}$ for [Au(IPr)(Seu)]PF$_6$ due to C—H stretching vibrations of IPr were also observed.

The $^1$H and $^{13}$C NMR chemical shifts of the complexes are given in Tables 1 and 2 respectively. The values for [Au(Ipr)Cl] are close to those reported in the literature and are presented here for comparison. See M. Altaf, M. Monim-ul-Mehboob, A. A. Seliman, A. A. Isab, V. Dhuna, G. Bhatia, K. Dhuna, Synthesis, X-ray Structures, Spectroscopic Analysis and Anticancer Activity of Novel Gold(I) Carbene Complexes, J, Organomet. Chem. 765 (2014) 68-79; and M. R. Fructos, et al., incorporated herein by reference in their entirety. The $^1$H chemical shifts associated with IPr part of Complex (1) fall in nearly the same region as observed for [Au(Ipr)Cl]. However, the N—H resonance of Seu in Complex 1 shifted downfield by about 0.6 ppm compared to its value in the free state. In $^{13}$C NMR of [Au(IPr)(Seu)]PF$_6$ or Complex (I), the carbene carbon resonance shifted downfield by 10 ppm with respect to its position in [Au(IPr)Cl]. The downfield shift is consistent with the transfer of electron density from carbon to metal atom upon coordination. The other resonances of IPr ligand remained almost unchanged. On the other hand, the C=Se resonance in [Au(IPr)(Seu)]PF$_6$ appeared upfield by 9 ppm compared to that in uncoordinated Seu. This upfield shift is in accordance with the literature data. See Ahmad, A. A. Isab, A. R. Al-Arfaj and A. P. Arnold, Synthesis of cyano (selenone)gold(I) complexes and investigation of their scrambling reactions using $^{13}$C and $^{15}$N NM R spectroscopy, Polyhedron 21 (2002) 2099-2105; S. Ahmad, A. A. Isab, Silver(I) complexes of selenourea ($^{13}$C and $^{15}$N labeled); characterization by $^{13}$C, and $^{15}$N and $^{107}$Ag NMR, Inorg. Chem. Commun. 5 (2002) 355-357, A, A, Isab, M. I. M, Wazeer, M. Fettouhi, S. Ahmad, W. Ashraf, Synthesis and Characterization of Mercury(II) Complexes of Selones; X-ray Structure, CP MAS and Solution NMR Studies, Polyhedron 25 (2006) 2629-2636; and A. Ahmad, A. A. Isab, Mixed ligand gold(I) complexes with phosphines and selenourea, Transition Metal Chemistry 28 (2003) 50-543, each incorporated herein by reference in their entirety.

In $^{77}$Se NMR the coordination of Seu with gold(I) shifts the signal significantly upfield by more than 45 ppm ($\delta^{77}$Se=154.2 ppm in Complex (I) Vs $\delta^{77}$Se=200.7 ppm in Seu). This very large shielding appears to be the characteristic of gold(I) binding to the selenium of Seu. This observation is consistent with the data of our previous studies. See S. Ahmad, A. A. Isab, Silver(I) complexes of selenourea ($^{13}$C and $^{15}$N labeled); characterization by $^{13}$C, $^{15}$N and $^{107}$Ag NMR, Inorg. Chem. Commun. 5 (2002) 355-357; A. A. Isab et al.; and A. Ahmad et al., each incorporated herein by reference in their entirety.

TABLE 1

$^1$H NMR chemical shifts (ppm) of Seu and gold(I) complexes in CDCl$_3$.

| Compound | H-3 | H-4 | H-5 | H-6 | H-7 | H-8 | N—H |
|---|---|---|---|---|---|---|---|
| [Au(Ipr)Cl] | 7.39 d | 7.55 t | 2.46 m | 1.33 d | 1.21 d | 7.98 s | — |
| [Au(Ipr)(Seu]PF$_6$ | 7.36 d | 7.57 t | 2.56 m | 1.32 d | 1.26 d | 7.88 s | 8.12 |
| Seu | — | — | — | — | — | — | 7.54 |

TABLE 2

$^{13}$C NMR chemical shifts (ppm) for Seu and gold(I) complexes in CDCl$_3$.

| Compound | C1 | C2 | C3 | C4 | C5 | C6 | C7 | C8 | C—Au | C=Se |
|---|---|---|---|---|---|---|---|---|---|---|
| [Au(Ipr)Cl] | 145.5 | 130.7 | 133.9 | 124.2 | 28.8 | 24.5 | 24.0 | 123.0 | 175.3 | — |
| 1 | 145.8 | 131.6 | 133.9 | 124.2 | 28.8 | 24.5 | 23.8 | 123.5 | 185.3 | 173.2 |
| Seu | — | — | — | — | — | — | — | — | — | 182.2 |

Figure 2:
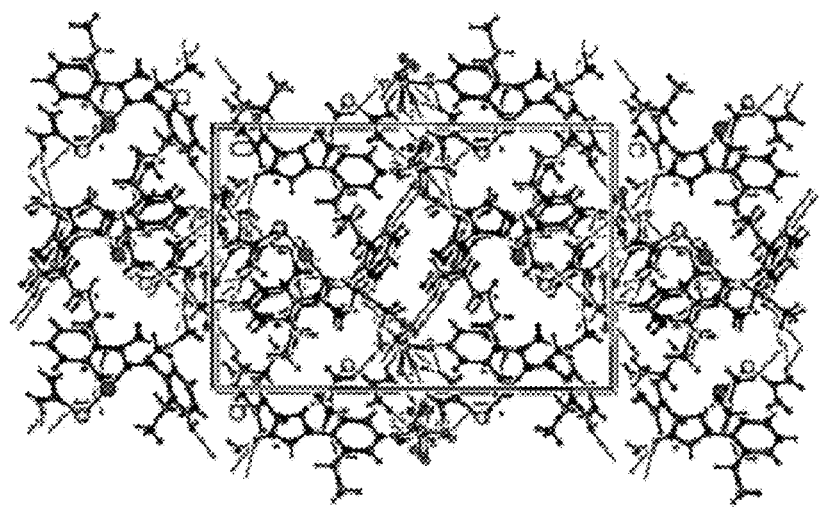
FIG. 2. The crystal packing of [Au(Ipr)(Seu)]PF$_6$ (1) viewed along the a axis.

The molecular structure and crystal packing of [Au(Ipr) (Seu)]PF$_6$ or Complex (I) are depicted in FIGS. 1 and 2 respectively. The selected bond lengths and angles are given in Table 3. The gold(I) atom in Complex (I) is two-coordinate in a nearly linear environment with the C—Au—Se bond angle of 177.39(9)°. The Au—C bond length (2.005(3) Å) falls in the range observed for other gold(I)-carbene complexes, while Au—Se bond length (2.4089(6) Å) is somewhat shorter than that observed in the analogous phosphine complexes ((2.4360(6) Å [Me$_3$P—Au-Seu]$_2$Cl$_2$ and 2.412(2) Å for [Ph$_3$P—Au-Seu]Cl). See P. J. Barnard, M. V. Baker, S. J. Berners-Price, B. W. Skelton, A. H. White, Dinuclear gold(I) complexes of bridging bidentate carbene ligands: synthesis, structure and spectroscopic characterization, Dalton Trans. (2004) 1038-1047; H. G. Raubenheimer et al.; M. Z. Ghdhayeb et al.; E. Deck et al.; P. de Fremont et al.; M. R. Fructos et al.; S. Gaillard et al.; A. Gomez-Suarez et al; M. Fettouhi, M. I. M. Wazeer, S. Ahmad, A. A. Isab, X-ray structure and $^{77}$Se, $^{31}$P and $^{13}$C MAS NMR of the dinuclear complex 1,2-bis(selenourea)-1kSe, 2kSe-1,2-bis(trimethylphosphine)digold(I) chloride, Polyhedron 23 (2004) 1-4; and P. G. Jones, C. Thone, Gold Complexes with Selenium Ligands, IV Preparation, Crystal Structures and Reactions of Phosphine(selenourea)gold(I) Complexes, Chem. Ber 124 (1991) 2725, each incorporated herein by reference in their entirety. The slightly shorter Au—Se bond suggests the stronger π-accepting ability of Seu in the presence of a carbene coordinated to gold. The complex exists in the monomeric form similar to [Ph$_3$P—Au-Seu]Cl. See P. G. Jones et al., incorporated herein by reference in its entirety. On the other hand, [Me$_3$P—Au-Seu]$_2$Cl$_2$ is a dinuclear complex assembled through aurophilic interac (Au—Au=3.0386(5) Å). See M. Fettouhi et al., incorporated herein by reference in its entirety. In the case of Complex (I) as well as [Ph$_3$P—Au-Seu]Cl, the dimerization is probably hindered by the steric effect of the bulky ligands. The C—Se bond length in Complex (I) is slightly longer, while the C—N distance is shorter than in the free Seu ligand (1.86(2) and 136 Å respectively). See J. S. Rutherford, C. Calvo. The crystal structure of selenourea, Z. Kristallogr, 128 (1969) 229-258 incorporated herein by reference in its entirety. This observation is related to the N→C(Se) shift of electron density upon coordination and is consistent with the spectroscopic data. The bond angles around SeCN2 fragment of Seu represent a trigonal planar environment. The complex cation and PF$_6^-$ anion are associated with each other through electrostatic interactions. See FIG. 1.

TABLE 3

Selected bond distances (Å) and bond angles (°) for Complex (1).

| Bond Distance | | Bond angles | |
|---|---|---|---|
| Au1—C2 | 2.005 (3) | Se1—Au1—C2 | 177.39 (9) |
| An1—Se1 | 2.4089 (6) | Au1—Se1—C1 | 99.67 (14) |
| Se1—C1 | 2.883 (4) | N1—C1—N2 | 119.80 (4) |
| N1—C1 | 1.308 (6) | Se1—C1—N1 | 118.60 (3) |
| N2—C1 | 1.320 (7) | Se1—C1—N2 | 121.50 (3) |

The complexes, [Au(Ipr)Cl] and [Au(Ipr)(Seu)]PF$_6$ or Complex (I), as well as cisplatin (standard anticancer drug) were tested for in vitro cytotoxicity against three human cancer cell lines; A549 (lung carcinoma), HCT15 (colon cancer cells) and MCF7 (breast cancer cells) using MTT assay.

Figure 3A:
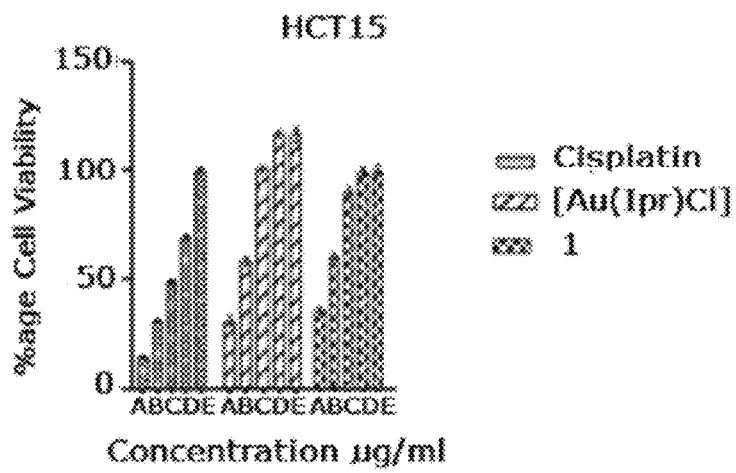
FIGS. 3A, 3B and 3C describe survival of the cells as a function of concentration of the complexes.
Figure 3B:
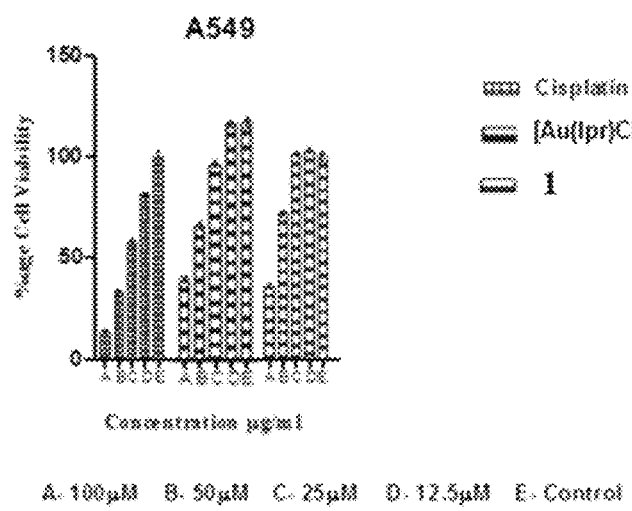
Figure 3C:
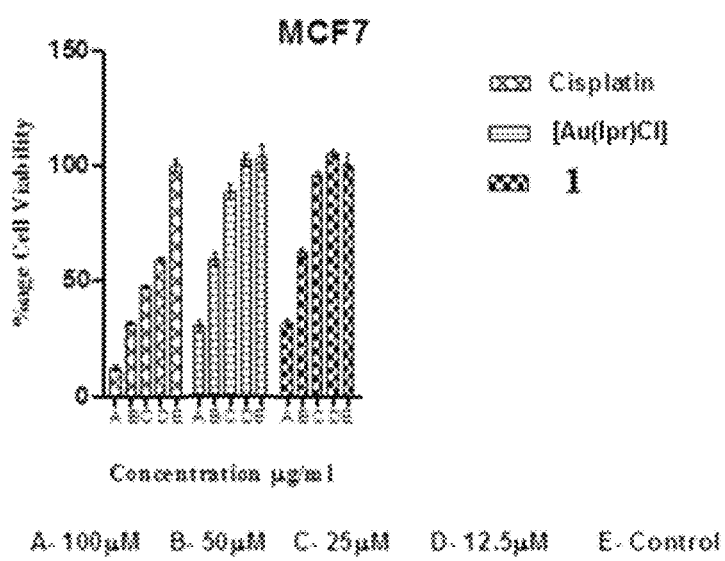

The IC$_{50}$ values (as µM) obtained from the plot of the concentration of compounds against the percentage of cell viability are given in Table 4. The dose-dependent inhibition of cell proliferation was obtained by a specific increase m the concentration of cisplatin and gold complexes against a fixed number of three human cancer cell lines as illustrated in FIG. 3. The data in Table 4 showed that the gold complexes with higher IC$_{50}$ values were less effective than cisplatin in inhibiting the growth of cancer cells in all cases. However, Complex (I) is more active than [Au(IPr)Cl].

The greater activity of Complex (I) compared to [Au(IPr) Cl] suggests that the binding of Seu increases the inhibition efficiency of the gold(I) complex. This may be due to the ionic nature of the complex that favors its aqueous solubility. The effectiveness of the complexes is almost same for the three cells.

TABLE 4

IC$_{50}$ values (µM) of gold(I) complexes against HCT15, A549 and MCF7 cancer cell lines

| Complex | HCT15 | A549 | MCF7 |
|---|---|---|---|
| Cisplatin | 32 ± 2 | 42 ± 2 | 23 ± 4 |
| [Au(Ipr)Cl] | 122 ± 1 | 180 ± 2 | 110 ± 2 |
| 1 | 76 ± 2 | 82 ± 1 | 75 ± 3 |

Figure 4:
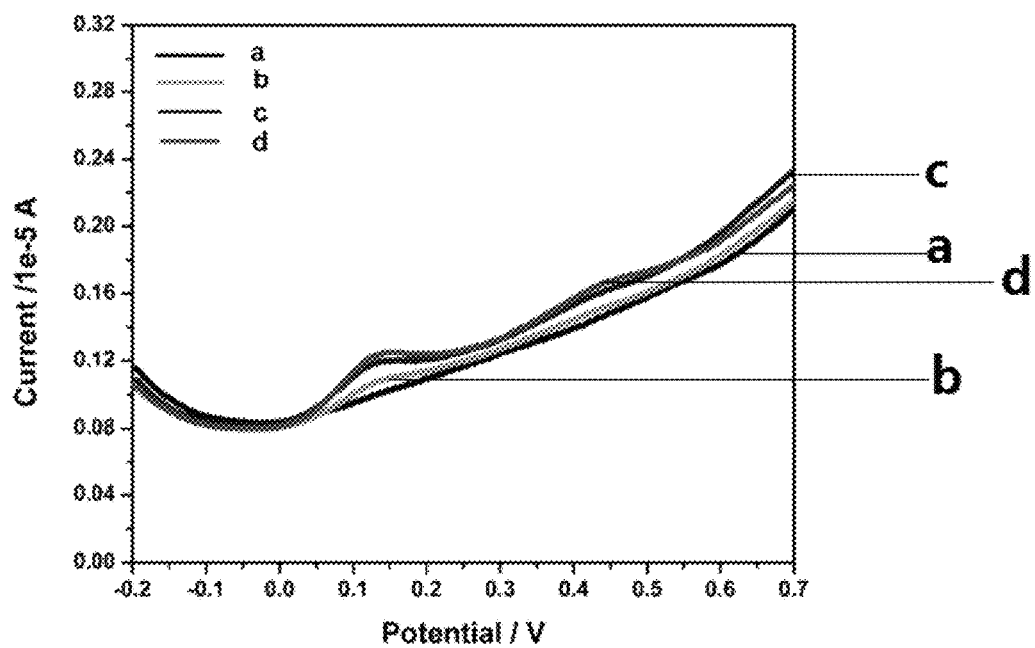
FIG. 4. SWS voltammograms in a 0.1 M phosphate buffer aqueous solution (2.0 mL) at GCE (a) and in the presence of 0.20 mL 50.0 μM (b), 0.30 mL, 75.0 μM (e) and 0.40 mL, 100.0 μM (d) of the complex.

The stability and electrochemical behavior of complex 1 were examined by its electroactive properties in phosphate buffer solution of pH 7.0 using SWSV technique (Square wave stripping voltammetry). In order to obtain the best electrochemical response, a preliminary study was carried out using relevant reference solutions (phosphate buffer aqueous solution and methanol). Two oxidized peaks on the surface of a glassy carbon electrode (GCE) at about 0.15 V and 0.40 V were observed for complex 1 as shown in FIG. 4. These peaks may likely be the result of free electron transfer from the solution of the complex to the surface of the electrode by applying potential. Intensities of both peaks were observed to raise with the presence of 2.0 mL of 50, 75 and 100 µMs concentrations of Complex (I) in 0.1 M phosphate buffer (pH 7.0). The complete solubility of the studied concentrations of the complex in the medium is responsible for the increase in peak height with an estimation of 8.53 mg/100 ml solubility of Complex (I), in phosphate buffer based on the highest soluble concentration. The perseverance of peaks at different concentration levels is an evidence of the stability of the complex.

Figure 5A:
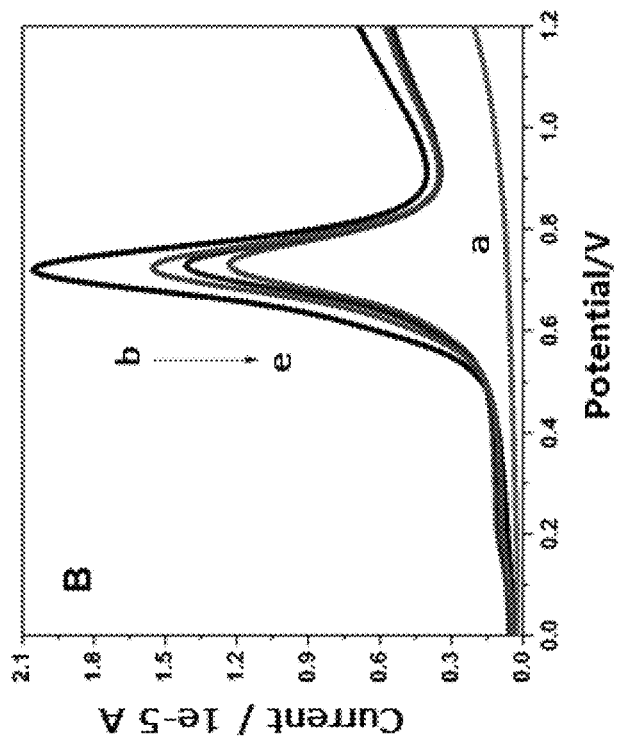
FIGS. 5A and 5B. SWS voltammograms in 0.1 M phosphate buffer (pH 7.0) aqueous solution (2.0 mL) at a GCE surface in absence (a) and presence (b) of 0:10 mL, 500 μM L-tyrosine (FIG. 5A) or L-tryptophan (FIG. 5B) and subsequent additions of (c) 0.20 mL, 50 μM, (d) 0.30 mL, 75 μM and (e) 0.40 mL, 100 μM of the complex.
Figure 5B:
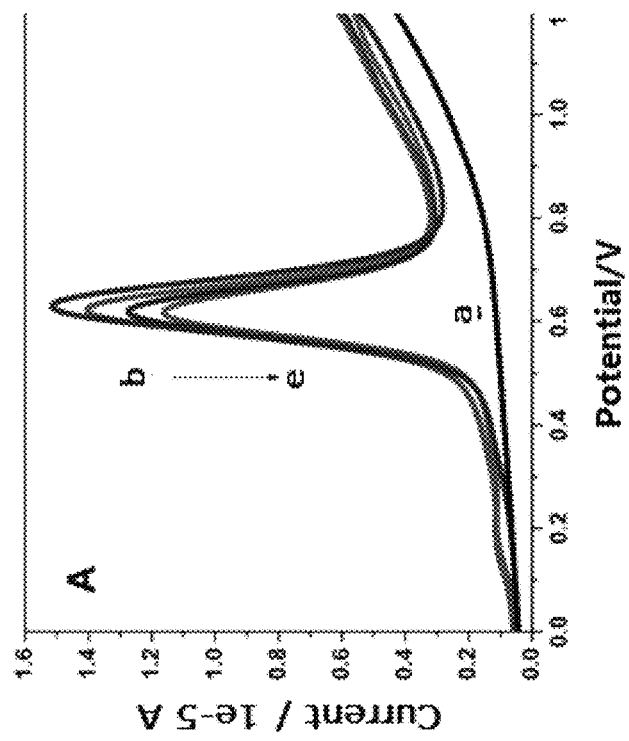

Voltammograms obtained for the interaction studies of the Complex (I), with L-tyrosine and L-tryptophan are shown in FIG. 5. The height of both L-tyrosine and L-tryptophan peaks were observed to decrease as different concentrations of the complex were added. Reductions in the peak height of both amino acids could be related to the degree of their interactions with the Au center in the complex. The electrodecomposition potential values of both amino acids remained nearly constant despite their interaction with the complex.

As a control experiment, the SWS response of L-tyrosine and L-tryptophan retained the same peak current intensity and peak shape even after spiking the same volume of the solvent blank used to prepare the complex solution in the interaction study.

As shown herein, the inventors describe the first crystal structure and spectral characterization of an adduct formed between gold(I)-carbene compound and selenourea, namely [Au(IPr)(Seu)]PF$_6$ or Complex (I). They have also found that the complex is stable in aqueous solution and that it favorably interacts with L-tyrosine and L-tryptophan. Moreover, the inventors describe the cytotoxic activity of this complex against A549, HCT15, and MCF7 human cancer cell lines.

Terminology

Terminology used herein is for the purpose of describing particular embodiments only and is not intended to be limiting of the invention.

The headings (such as "Background" and "Summary") and sub-headings used herein are intended only for general organization of topics within the present invention, and are not intended to limit the disclosure of the present invention or any aspect thereof. In particular, subject matter disclosed in the "Background" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

As used herein, the words "a" and "an" and the like carry the meaning of "one or more" unless the context clearly indicates otherwise.

Within the description this disclosure, where a numerical limit or range is stated, the endpoints are included unless stated otherwise. Also, all values and subranges within a numerical limit or range are specifically included as if explicitly written out.

The terms "including", "such as", "for example" and the like not intended to limit the scope of the present disclosure. They generally refer to one or more elements falling with a class or genus of other similar elements.

It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

As used herein, the term "and/or" includes any and all combinations of one or more of the associated listed items and ma be abbreviated as "/".

Links are disabled by deletion of http: or by insertion of a space or underlined space into In some instances, the text available via the link on the "last accessed" date may be incorporated by reference.

As used herein in the specification and claims, including as used in the examples and unless otherwise expressly specified, all numbers may be read as if prefaced by the word "substantially", "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/− 0.1% of the stated value (or range of values), +/− 1% of the stated value (or range of values), +/− 2% of the stated value (or range of values), +/− 5% of the stated value (or range of values), +/− 10% of the stated value (or range of values), +/− 15% of the stated value (or range of values), +/− 20% of the stated value (or range of values), etc. Any numerical ranue recited herein is intended to include all sub-ranges subsumed therein.

Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10 it also describes subranges for Parameter X including 1-9, 1-8, 1-7, 2-9, 2-8, 2-7, 3-9, 3-8, 3-7, 2-8, 3-7, 4-6, or 7-10, 8-10 or 9-10 as mere examples, range encompasses its endpoints as well as values inside of an endpoint, for example, the range 0-5 includes 0, >0, 1, 2, 3, 4, <5 and 5.

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology. As referred to herein, all compositional percentages are by weight of the total composition, unless otherwise specified. As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present invention that do not contain those elements or features.

Although the terms "first" and "second" may be used herein, to describe yank features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and, use the compositions and methods of this technology and, unless explicitly stated otherwise are not intended to be a representation that given embodiments of this technology have, or have not, been made or tested.

All publications and patent applications mentioned in this specification are herein incorporated by reference in their entirety to the same extent as if each individual publication or patent application was specifically and individually indicated to be incorporated by reference, especially referenced is disclosure appearing in the same sentence, paragraph, page or section of the specification in which the incorporation by reference appears.

The citation of references herein does not constitute an admission that those references are prior art or have any relevance to the patentability of the technology disclosed herein. Any discussion of the content of references cited is intended merely to provide a general summary of assertions made by the authors of the references, and does not constitute an admission as to the accuracy of the content of such references.

The invention claimed is:

1. A method for treating a proliferative disease, disorder or condition in a subject, comprising:
administering to a subject in need thereof a composition comprising [Au(Ipr)(Seu)][anion] (1), wherein Ipr is 1,3-bis(2,6-di-isopropylphenyl)imidazol-2-ylidene, and Seu is selenourea, as described by Formula (3):

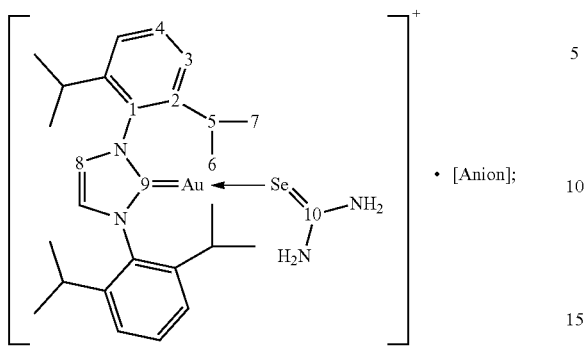

Formula (3)

wherein the proliferative disease, disorder, or condition is breast cancer, colon cancer or lung cancer.

2. The method of claim 1, wherein the anion is $PF_6^-$.

3. The method of claim 1, wherein the proliferative disease, disorder, or condition is breast cancer.

4. The method of claim 1, wherein the proliferative disease, disorder, or condition is colon cancer.

5. The method of claim 1, wherein the proliferative disease, disorder, or condition is lung cancer.

* * * * *